(12) United States Patent
Messinger et al.

(10) Patent No.: US 9,710,573 B2
(45) Date of Patent: Jul. 18, 2017

(54) INSPECTION DATA GRAPHICAL FILTER

(71) Applicant: General Electric Company, Schenectady, NY (US)

(72) Inventors: Jason Howard Messinger, Andover, MA (US); Charles Burton Theurer, Alplaus, NY (US); Thomas Eldred Lambdin, Auburn, NY (US); Michael Christopher Domke, Skaneateles, NY (US); Sekhar Soorianarayanan, Bangalore (IN); Scott Leo Sbihli, Lexington, MA (US)

(73) Assignee: General Electric Company, Schenectady, NY (US)

( * ) Notice: Subject to any disclaimer, the term of this patent is extended or adjusted under 35 U.S.C. 154(b) by 561 days.

(21) Appl. No.: 13/747,435

(22) Filed: Jan. 22, 2013

(65) Prior Publication Data

US 2014/0207419 A1 Jul. 24, 2014

(51) Int. Cl.
| | | |
|---|---|---|
| *G06T 15/40* | (2011.01) | |
| *G06F 17/50* | (2006.01) | |
| *G01N 27/90* | (2006.01) | |
| *G01N 29/04* | (2006.01) | |
| *G01N 29/44* | (2006.01) | |
| *G01N 23/02* | (2006.01) | |
| *G01N 21/954* | (2006.01) | |

(Continued)

(52) U.S. Cl.
CPC ........... *G06F 17/50* (2013.01); *G01N 21/954* (2013.01); *G01N 23/02* (2013.01); *G01N 27/90* (2013.01); *G01N 29/043* (2013.01); *G01N 29/4472* (2013.01); *G06F 11/32* (2013.01); *G06T 19/20* (2013.01); *G01N 2223/631* (2013.01); *G01N 2223/646* (2013.01); *G01N 2291/2693* (2013.01); *G01N 2291/2694* (2013.01); *G06T 2219/004* (2013.01); *G06T 2219/2012* (2013.01)

(58) Field of Classification Search
CPC ......... G06F 17/50; G06F 11/32; G01N 27/90; G01N 29/043; G01N 29/4472; G01N 23/02; G01N 21/954; G01N 2291/2694; G01N 2223/631; G01N 2223/646
See application file for complete search history.

(56) References Cited

U.S. PATENT DOCUMENTS 6,317,039 B1 11/2001 Thomason
6,830,545 B2 12/2004 Bendall
(Continued)

OTHER PUBLICATIONS

Sorrel, Charlie. iControlPad Ships at Last [online], [retrieved on Mar. 21, 2013]. Retrieved from the Internet <URL: http://www.wired.com/gadgetlab/2011/11/icontrolpad-ships-at-last/>.
(Continued)

*Primary Examiner* — Robert Craddock
(74) *Attorney, Agent, or Firm* — Fletcher Yoder, P.C.

(57) ABSTRACT

A system is provided that includes computer-readable storage configured to store non-destructive testing inspection data relating to a portion of an object that has been inspected. Further, a processor presents a model associated with the object, associates the inspection data with the related portion of the object; and presents an indication of availability of the inspection data on a portion of the presented model. The portion of the presented model relates to the portion of the object associated with the inspection data.

20 Claims, 17 Drawing Sheets

(51) Int. Cl.
*G06F 11/32* (2006.01)
*G06T 19/20* (2011.01)

(56) References Cited

U.S. PATENT DOCUMENTS

| | | | |
|---|---|---|---|
| 8,059,882 | B2 | 11/2011 | Amidi |
| 8,108,168 | B2 | 1/2012 | Sharp et al. |
| 8,255,170 | B2 | 8/2012 | Kollgaard et al. |
| 8,443,301 | B1 * | 5/2013 | Easterly .............. G01M 17/007 715/848 |
| 2002/0198997 | A1 | 12/2002 | Linthicum et al. |
| 2005/0031195 | A1 * | 2/2005 | Liu ............................... 382/154 |
| 2007/0010923 | A1 | 1/2007 | Rouyre |
| 2007/0217672 | A1 | 9/2007 | Shannon et al. |
| 2008/0247635 | A1 | 10/2008 | Davis et al. |
| 2009/0136114 | A1 | 5/2009 | Wu et al. |
| 2009/0210814 | A1 | 8/2009 | Agrusa et al. |
| 2009/0307628 | A1 | 12/2009 | Metala et al. |
| 2011/0298800 | A1 | 12/2011 | Schlichte et al. |

OTHER PUBLICATIONS

OmniScan MX [online]. p. 5. Olympus, 2010 [retrieved on Mar. 28, 2013]. Retrieved from the Internet: <URL: www.olympus-ims.com/en/omniscan-mx/>.

Georgeson, Gary. [online], [retrieved on Mar. 28, 2013]. http://www.meetingdata.utcdayton.com/agenda/airworthiness/2012/proceedings/presentations/P5526.pdf.

Phasor XS User's Manual [online]. General Electric: Measurement & Control Solutions. [retrieved on Mar. 28, 2013]. Retrieved from the Internet: <URL: www.ge-mcs.com/download/ultrasound/portable-flaw-detectors/Phasor%20Series/om-phasor-en__rev10.pdf>.

USM Vision 1.2—A Total Weld Inspection Solution to Increase Productivity in New Process Pipework Fabrication [online]. General Electric: Measurement & Control. [retrieved on Mar. 28, 2013]. Retrieved from the Internet: <URL: www.ge-mcs.com/download/ultrasound/portable-flaw-detectors/usm-vision/GEIT-USMVision-20058EN__LR.pdf>.

U.S. Appl. No. 13/747,438, filed Jan. 22, 2013, Jason Howard Messinger.
U.S. Appl. No. 13/747,457, filed Jan. 22, 2013, Jason Howard Messinger.
U.S. Appl. No. 13/747,453, filed Jan. 22, 2013, Sekhar Soorianarayanan.
U.S. Appl. No. 13/747,429, filed Jan. 22, 2013, Sekhar Soorianarayanan.
U.S. Appl. No. 13/747,464, filed Jan. 22, 2013, Sekhar Soorianarayanan.
U.S. Appl. No. 13/747,443, filed Jan. 22, 2013, Jason Howard Messinger.
U.S. Appl. No. 13/747,449, filed Jan. 22, 2013, Michael Christopher Domke.
U.S. Appl. No. 13/747,456, filed Jan. 22, 2013, Michael Christopher Domke.
U.S. Appl. No. 13/747,416, filed Jan. 22, 2013, Michael Christopher Domke.
U.S. Appl. No. 13/747,408, filed Jan. 22, 2013, Michael Christopher Domke.
U.S. Appl. No. 13/800,015, filed Mar. 13, 2013, Kevin Andrew Coombs.
U.S. Appl. No. 13/747,408, filed Dec. 31, 2012, Michael Christopher Domke.
U.S. Appl. No. 13/732,252, filed Dec. 31, 2012, Kevin Andrew Coombs.
U.S. Appl. No. 13/732,261, filed Dec. 31, 2012, Eugene Schiefer.
U.S. Appl. No. 13/732,281, filed Dec. 31, 2012, Jason Howard Messinger.
U.S. Appl. No. 13/732,293, filed Dec. 31, 2012, Jason Howard Messinger.
U.S. Appl. No. 13/732,303, filed Dec. 31, 2012, Thomas Eldred Lambdin.
U.S. Appl. No. 13/732,268, filed Dec. 31, 2012, Scott Leo Sbihli.
U.S. Appl. No. 13/732,309, filed Dec. 31, 2012, Jason Howard Messinger.
U.S. Appl. No. 13/732,272, filed Dec. 31, 2012, Jason Howard Messinger.
U.S. Appl. No. 13/732,319, filed Dec. 31, 2012, Kevin Andrew Coombs.
U.S. Appl. No. 13/732,327, filed Dec. 31, 2012, Kevin Andrew Coombs.
European Search Report and Opinion issued in connection with corresponding EP Application No. 13826679.6 on Aug. 4, 2016.
International Search Report and Written Opinion issued in connection with corresponding Application No. PCT/US2013/075900 on Oct. 20, 2014.

* cited by examiner

INSPECTION DATA GRAPHICAL FILTER

BACKGROUND

The subject matter disclosed herein relates to presenting inspection data. More specifically, the subject matter disclosed herein relates to sorting and/or providing inspection data using a graphical filter.

Certain equipment and facilities, such as power generation equipment and facilities, oil and gas equipment and facilities, aircraft equipment and facilities, manufacturing equipment and facilities, and the like, include a plurality of interrelated systems, and processes. For example, power generation plants may include turbine systems and processes for operating and maintaining the turbine systems. Likewise, oil and gas operations may include carbonaceous fuel retrieval systems and processing equipment interconnected via pipelines. Similarly, aircraft systems may include airplanes and maintenance hangars useful in maintaining airworthiness and providing for maintenance support. During equipment operations, the equipment may degrade, encounter undesired conditions such as corrosion, wear and tear, and so on, potentially affecting overall equipment effectiveness. Certain inspection techniques, such as non-destructive inspection techniques or non-destructive testing (NDT) techniques, may be used to detect undesired equipment conditions.

NDT relates to the examination of an object, material, or system without reducing future usefulness. In particular NDT inspections may be used to determine the integrity of a product using time-sensitive inspection data relating to a particular product. For example, NDT inspections may observe the "wear and tear" of a product over a particular time-period.

Many forms or modalities of NDT are currently known. For example, perhaps the most common NDT method is visual examination. During a visual examination, an inspector may, for example, simply visually inspect an object for visible imperfections. Alternatively, visual inspections may be conducted using optical technologies such as a computer-guided camera, a borescope, etc. Radiography is another form of NDT. Radiography relates to using radiation (e.g., x-rays and/or gamma rays) to detect thickness and/or density changes to a product, which may denote a defect in the product. Further, ultrasonic testing relates to transmitting high-frequency sound waves into a product to detect changes and/or imperfections to the product. Using a pulse-echo technique, sound it introduced into the product and echoes from the imperfections are returned to a receiver, signaling that the imperfection exists. Many other forms of NDT exist. For example, magnetic particle testing, penetrant testing, electromagnetic testing, leak testing, and acoustic emission testing, to name a few.

Oftentimes, product inspections may be quite complex due to the complex nature of the product being tested. For example, airplanes are very complex machines where safety and inspection standards are of the utmost importance. The Boeing 777 aircraft may have as many 3 million parts. Accordingly, a tremendous amount of time and effort is used to inspect these aircraft on a periodic basis. Further, historical data relating to previous inspections may be used to compare and contrast inspection results to understand trending data. Further, inspection data for an entire fleet of products (e.g., a fleet of Boeing 777's) may be useful for inspection purposes. As may be appreciated, massive amounts of data may be gathered and used in the inspection process.

Unfortunately, in conventional inspection systems, the presentation of data may inundate NDT operators or personnel with a massive amount of information regarding inspection. As increased inspection data is provided to these inspection systems, it may become increasingly difficult to filter inspection data in an efficient way, such that targeted data may be accessed. Accordingly, improved systems and methods for filtering inspection data are desirable.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, a method is provided. A processor is used to obtain a computer-presentable model relating to an object being inspected. The processor determines a portion of model relating to a portion of the object to be inspected. An inspection tool inspects the portion of the object to gather inspection data and the processor associates an indicator of the portion of the model with the gathered inspection data.

In a second embodiment, a system is provided. The system includes computer-readable storage configured to store non-destructive testing inspection data relating to a portion of an object that has been inspected. Further, a processor presents a model associated with the object, associates the inspection data with the related portion of the object; and presents an indication of availability of the inspection data on a portion of the presented model. The portion of the presented model relates to the portion of the object associated with the inspection data.

In a third embodiment, a tangible, non-transitory, machine-readable medium, includes machine-readable instructions to present a model associated with the object, associate the inspection data with the related portion of the object; and present an indication of availability of the inspection data on a portion of the presented model, where the portion of the presented model relates to the portion of the object associated with the inspection data.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
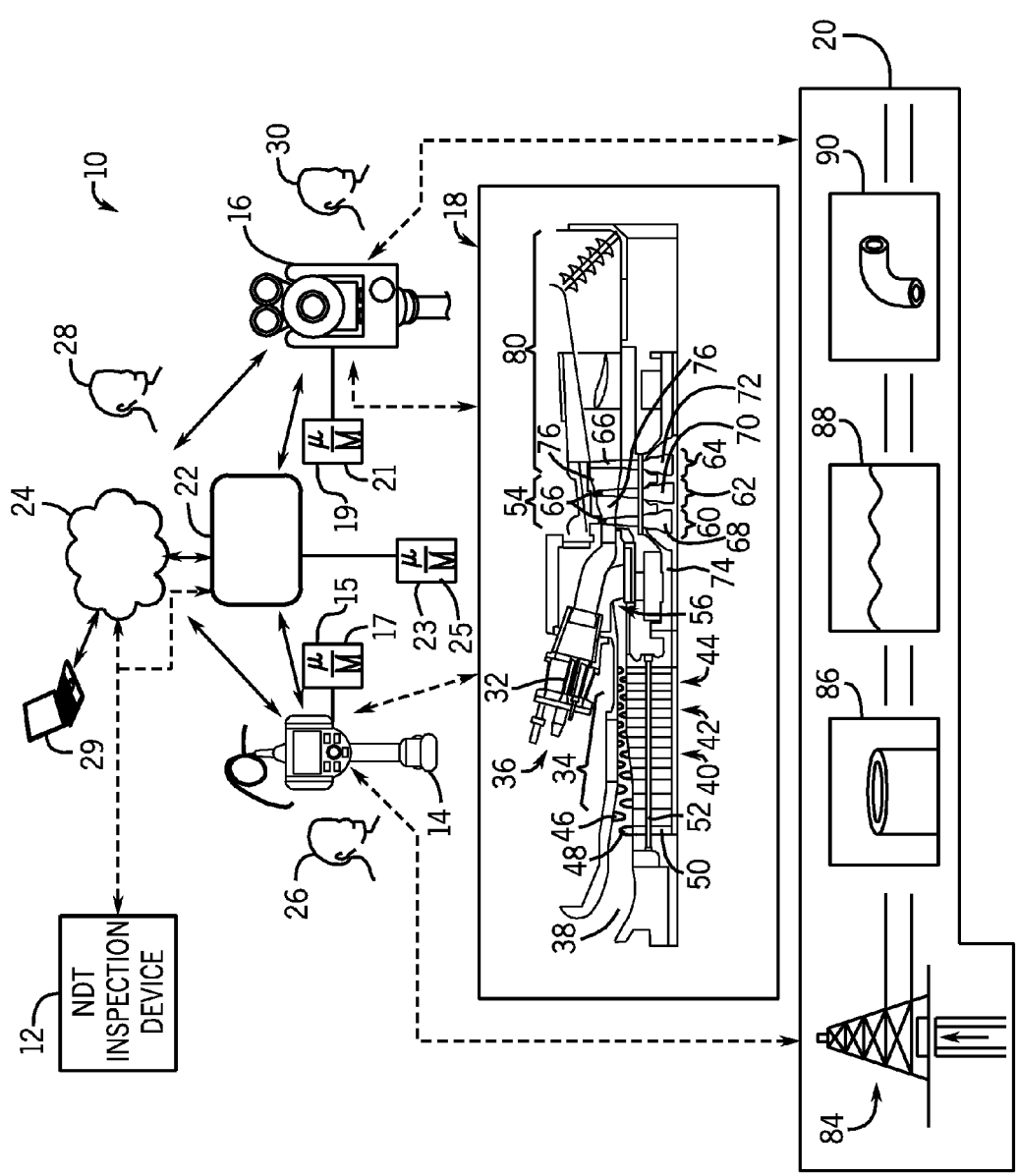
FIG. 1 is a block diagram illustrating an embodiment of a distributed non-destructive testing (NDT) system, including a mobile device.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Embodiments of the present disclosure may apply to a variety of inspection and testing techniques, including non-destructive testing (NDT) or inspection systems. In the NDT system, certain techniques such as borescopic inspection, weld inspection, remote visual inspections, x-ray inspection, ultrasonic inspection, eddy current inspection, and the like, may be used to analyze and detect a variety of conditions, including but not limited to corrosion, equipment wear and tear, cracking, leaks, and so on. The techniques described herein provide for improved NDT systems suitable for borescopic inspection, remote visual inspections, x-ray inspection, ultrasonic inspection, and/or eddy current inspection, enabling enhanced data gathering, data analysis, inspection/testing processes, and NDT collaboration techniques.

The improved NDT systems described herein may include inspection equipment using wireless conduits suitable for communicatively coupling the inspection equipment to mobile devices, such as tablets, smart phones, and augmented reality eyeglasses; to computing devices, such as notebooks, laptops, workstations, personal computers; and to "cloud" computing systems, such as cloud-based NDT ecosystems, cloud analytics, cloud-based collaboration and workflow systems, distributed computing systems, expert systems and/or knowledge-based systems. Indeed, the techniques described herein may provide for enhanced NDT data gathering, analysis, and data distribution, thus improving the detection of undesired conditions, enhancing maintenance activities, and increasing returns on investment (ROI) of facilities and equipment.

In one embodiment, a tablet may be communicatively coupled to the NDT inspection device (e.g., borescope, transportable pan-tilt-zoom camera, eddy current device, x-ray inspection device, ultrasonic inspection device), such as a MENTOR™ NDT inspection device, available from General Electric, Co., of Schenectady, N.Y., and used to provide, for example, enhanced wireless display capabilities, remote control, data analytics and/or data communications to the NDT inspection device. While other mobile devices may be used, the use of the tablet is apt, however, insofar as the tablet may provide for a larger, higher resolution display, more powerful processing cores, an increased memory, and improved battery life. Accordingly, the tablet may address certain issues, such as providing for improved visualization of data, improving the manipulatory control of the inspection device, and extending collaborative sharing to a plurality of external systems and entities.

Keeping the foregoing in mind, the present disclosure is directed towards sharing data acquired from the NDT system and/or control of applications and/or devices in the NDT system. Generally, data generated from the NDT system may be automatically distributed to various people or groups of people using techniques disclosed herein. Moreover, content displayed by an application used to monitor and/or control devices in the NDT system may be shared between individuals to create a virtual collaborative environment for monitoring and controlling the devices in the NDT system.

By way of introduction, and turning now to FIG. 1, the figure is a block diagram of an embodiment of distributed NDT system 10. In the depicted embodiment, the distributed NDT system 10 may include one or more NDT inspection devices 12. The NDT inspection devices 12 may be divided into at least two categories. In one category, depicted in FIG. 1, the NDT inspection devices 12 may include devices suitable for visually inspecting a variety of equipment and environments. In another category, described in more detail with respect to FIG. 2 below, the NDT devices 12 may include devices providing for alternatives to visual inspection modalities, such as x-ray inspection modalities, eddy current inspection modalities, and/or ultrasonic inspection modalities.

In the depicted first example category of FIG. 1, the NDT inspection devices 12 may include a borescope 14 having one or more processors 15 and a memory 17, and a transportable pan-tilt-zoom (PTZ) camera 16 having one or more processors 19 and a memory 21. In this first category of visual inspection devices, the bore scope 14 and PTZ camera 16 may be used to inspect, for example, a turbo machinery 18, and a facility or site 20. As illustrated, the bore scope 14 and the PTZ camera 16 may be communicatively coupled to a mobile device 22 also having one or more processors 23 and a memory 25. The mobile device 22 may include, for example, a tablet, a cell phone (e.g., smart phone), a notebook, a laptop, or any other mobile computing device. The use of a tablet, however, is apt insofar as the tablet provides for a good balance between screen size, weight, computing power, and battery life. Accordingly, in one embodiment, the mobile device 22 may be the tablet mentioned above, that provides for touchscreen input. The mobile device 22 may be communicatively coupled to the NDT inspection devices 12, such as the bore scope 14 and/or the PTZ camera 16, through a variety of wireless or wired conduits. For example, the wireless conduits may include WiFi (e.g., Institute of Electrical and Electronics Engineers [IEEE] 802.11x), cellular conduits (e.g., high speed packet access [HSPA], HSPA+, long term evolution [LTE], WiMax), near field communications (NFC), Bluetooth, personal area networks (PANs), and the like. The wireless conduits may use a variety of communication protocols, such as TCP/IP, UDP, SCTP, socket layers, and so on. In certain embodiments, the wireless or wired conduits may include secure layers, such as secure socket layers (SSL), virtual private network (VPN) layers, encrypted layers, challenge key authentication layers, token authentication layers, and so on. Wired conduits may include proprietary cabling, RJ45 cabling, co-axial cables, fiber optic cables, and so on.

Additionally or alternatively, the mobile device 22 may be communicatively coupled to the NDT inspection devices 12, such as the borescope 14 and/or the PTZ camera 16, through the "cloud" 24. Indeed, the mobile device 22 may use the cloud 24 computing and communications techniques (e.g., cloud-computing network), including but not limited to HTTP, HTTPS, TCP/IP, service oriented architecture (SOA) protocols (e.g., simple object access protocol [SOAP], web services description languages (WSDLs)) to interface with the NDT inspection devices 12 from any geographic location, including geographic locations remote from the physical location about to undergo inspection. Further, in one embodiment, the mobile device 22 may provide "hot spot" functionality in which mobile device 22 may provide wireless access point (WAP) functionality suitable for connecting the NDT inspection devices 12 to other systems in the cloud 24, or connected to the cloud 24, such as a computing system 29 (e.g., computer, laptop, virtual machine(s) [VM], desktop, workstation). Accordingly, collaboration may be enhanced by providing for multi-party workflows, data gathering, and data analysis.

For example, a borescope operator 26 may physically manipulate the borescope 14 at one location, while a mobile device operator 28 may use the mobile device 22 to interface with and physically manipulate the bore scope 14 at a second location through remote control techniques. The second location may be proximate to the first location, or geographically distant from the first location. Likewise, a camera operator 30 may physically operate the PTZ camera 16 at a third location, and the mobile device operator 28 may remote control PTZ camera 16 at a fourth location by using the mobile device 22. The fourth location may be proximate to the third location, or geographically distant from the third location. Any and all control actions performed by the operators 26 and 30 may be additionally performed by the operator 28 through the mobile device 22. Additionally, the operator 28 may communicate with the operators 26 and/or 30 by using the devices 14, 16, and 22 through techniques such as voice over IP (VOIP), virtual whiteboarding, text messages, and the like. By providing for remote collaboration techniques between the operator 28 operator 26, and operator 30, the techniques described herein may provide for enhanced workflows and increase resource efficiencies. Indeed, nondestructive testing processes may leverage the communicative coupling of the cloud 24 with the mobile device 22, the NDT inspection devices 12, and external systems coupled to the cloud 24.

In one mode of operation, the mobile device 22 may be operated by the bore scope operator 26 and/or the camera operator 30 to leverage, for example, a larger screen display, more powerful data processing, as well as a variety of interface techniques provided by the mobile device 22, as described in more detail below. Indeed, the mobile device 22 may be operated alongside or in tandem with the devices 14 and 16 by the respective operators 26 and 30. This enhanced flexibility provides for better utilization of resources, including human resources, and improved inspection results.

Whether controlled by the operator 28, 26, and/or 30, the borescope 14 and/or PTZ camera 16 may be used to visually inspect a wide variety of equipment and facilities. For example, the bore scope 14 may be inserted into a plurality of borescope ports and other locations of the turbomachinery 18, to provide for illumination and visual observations of a number of components of the turbomachinery 18. In the depicted embodiment, the turbo machinery 18 is illustrated as a gas turbine suitable for converting carbonaceous fuel into mechanical power. However, other equipment types may be inspected, including compressors, pumps, turbo expanders, wind turbines, hydroturbines, industrial equipment, and/or residential equipment. The turbomachinery 18 (e.g., gas turbine) may include a variety of components that may be inspected by the NDT inspection devices 12 described herein.

With the foregoing in mind, it may be beneficial to discuss certain turbomachinery 18 components that may be inspected by using the embodiments disclosed herein. For example, certain components of the turbomachinery 18 depicted in FIG. 1, may be inspected for corrosion, erosion, cracking, leaks, weld inspection, and so on. Mechanical systems, such as the turbomachinery 18, experience mechanical and thermal stresses during operating conditions, which may require periodic inspection of certain components. During operations of the turbomachinery 18, a fuel such as natural gas or syngas, may be routed to the turbomachinery 18 through one or more fuel nozzles 32 into a combustor 36. Air may enter the turbomachinery 18 through an air intake section 38 and may be compressed by a compressor 34. The compressor 34 may include a series of stages 40, 42, and 44 that compress the air. Each stage may include one or more sets of stationary vanes 46 and blades 48 that rotate to progressively increase the pressure to provide compressed air. The blades 48 may be attached to rotating wheels 50 connected to a shaft 52. The compressed discharge air from the compressor 34 may exit the compressor 34 through a diffuser section 56 and may be directed into the combustor 36 to mix with the fuel. For example, the fuel nozzles 32 may inject a fuel-air mixture into the combustor 36 in a suitable ratio for optimal combustion, emissions, fuel consumption, and power output. In certain embodiments, the turbomachinery 18 may include multiple combustors 36 disposed in an annular arrangement. Each combustor 36 may direct hot combustion gases into a turbine 54.

As depicted, the turbine 54 includes three separate stages 60, 62, and 64 surrounded by a casing 76. Each stage 60, 62, and 64 includes a set of blades or buckets 66 coupled to a respective rotor wheel 68, 70, and 72, which are attached to a shaft 74. As the hot combustion gases cause rotation of turbine blades 66, the shaft 74 rotates to drive the compressor 34 and any other suitable load, such as an electrical generator. Eventually, the turbomachinery 18 diffuses and exhausts the combustion gases through an exhaust section 80. Turbine components, such as the nozzles 32, intake 38, compressor 34, vanes 46, blades 48, wheels 50, shaft 52, diffuser 56, stages 60, 62, and 64, blades 66, shaft 74, casing 76, and exhaust 80, may use the disclosed embodiments, such as the NDT inspection devices 12, to inspect and maintain said components.

Additionally, or alternatively, the PTZ camera 16 may be disposed at various locations around or inside of the turbomachinery 18, and used to procure visual observations of these locations. The PTZ camera 16 may additionally include one or more lights suitable for illuminating desired locations, and may further include zoom, pan and tilt techniques described in more detail below with respect to FIG. 4, useful for deriving observations around in a variety of difficult to reach areas. The borescope 14 and/or the camera 16 may be additionally used to inspect the facilities 20, such as an oil and gas facility 20. Various equipment such as oil and gas equipment 84, may be inspected visually by using the borescope 14 and/or the PTZ camera 16. Advantageously, locations such as the interior of pipes or conduits 86, underwater (or underfluid) locations 88, and difficult to observe locations such as locations having curves or bends 90, may be visually inspected by using the mobile device 22 through the borescope 14 and/or PTZ camera 16. Accordingly, the mobile device operator 28 may more safely and efficiently inspect the equipment 18, 84 and locations 86, 88, and 90, and share observations in real-time or near real-time with location geographically distant from the inspection areas. It is to be understood that other NDT inspection devices 12 may be use the embodiments described herein, such as fiberscopes (e.g., articulating fiberscope, non-articulating fiberscope), and remotely operated vehicles (ROVs), including robotic pipe inspectors and robotic crawlers.

Figure 2:
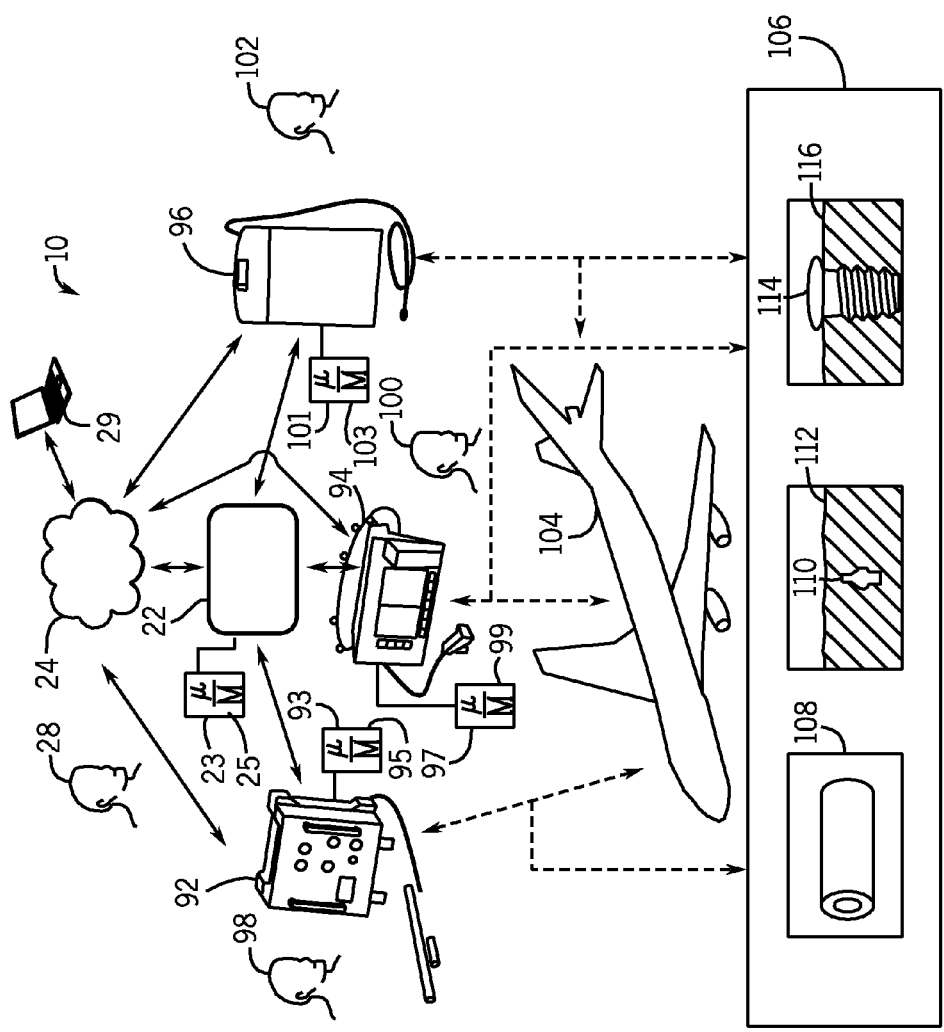
FIG. 2 is a block diagram illustrating further details of an embodiment of the distributed NDT system of FIG. 1.

Turning now to FIG. 2, the figure is a block diagram of an embodiment of the distributed NDT system 10 depicting the second category of NDT inspection devices 12 that may be able to provide for alternative inspection data to visual inspection data. For example, the second category of NDT inspection devices 12 may include an eddy current inspection device 92, an ultrasonic inspection device, such as an ultrasonic flaw detector 94, and an x-ray inspection device, such a digital radiography device 96. The eddy current inspection device 92 may include one or more processors 93 and a memory 95. Likewise, the ultrasonic flaw detector 94 may include one or more processors 97 and a memory 104. Similarly, the digital radiography device 96 may include one or more processors 101 and a memory 103. In operations, the eddy current inspection device 92 may be operated by an eddy current operator 98, the ultrasonic flaw detector 94 may be operated by an ultrasonic device operator 100, and the digital radiography device 96 may be operated by a radiography operator 102.

As depicted, the eddy current inspection device 92, the ultrasonic flaw detector 94, and the digital radiography inspection device 96, may be communicatively coupled to the mobile device 22 by using wired or wireless conduits, including the conduits mentioned above with respect to FIG. 1. Additionally, or alternatively, the devices 92, 94, and 96 may be coupled to the mobile device 22 by using the cloud 24, for example the borescope 14 may be connected to a cellular "hotspot," and use the hotspot to connect to one or more experts in borescopic inspection and analysis. Accordingly, the mobile device operator 28 may remotely control various aspects of operations of the devices 92, 94, and 96 by using the mobile device 22, and may collaborate with the operators 98, 100, and 102 through voice (e.g., voice over IP [VOIP]), data sharing (e.g., whiteboarding), providing data analytics, expert support and the like, as described in more detail herein.

Accordingly, it may be possible to enhance the visual observation of various equipment, such as an aircraft system 104 and facilities 106, with x-ray observation modalities, ultrasonic observation modalities, and/or eddy current observation modalities. For example, the interior and the walls of pipes 108 may be inspected for corrosion and/or erosion. Likewise, obstructions or undesired growth inside of the pipes 108 may be detected by using the devices 92, 94, and/or 96. Similarly, fissures or cracks 110 disposed inside of certain ferrous or non-ferrous material 112 may be observed. Additionally, the disposition and viability of parts 114 inserted inside of a component 116 may be verified. Indeed, by using the techniques described herein, improved inspection of equipment and components 104, 108, 112 and 116 may be provided. For example, the mobile device 22 may be used to interface with and provide remote control of the devices 14, 16, 92, 94, and 96.

Figure 3:
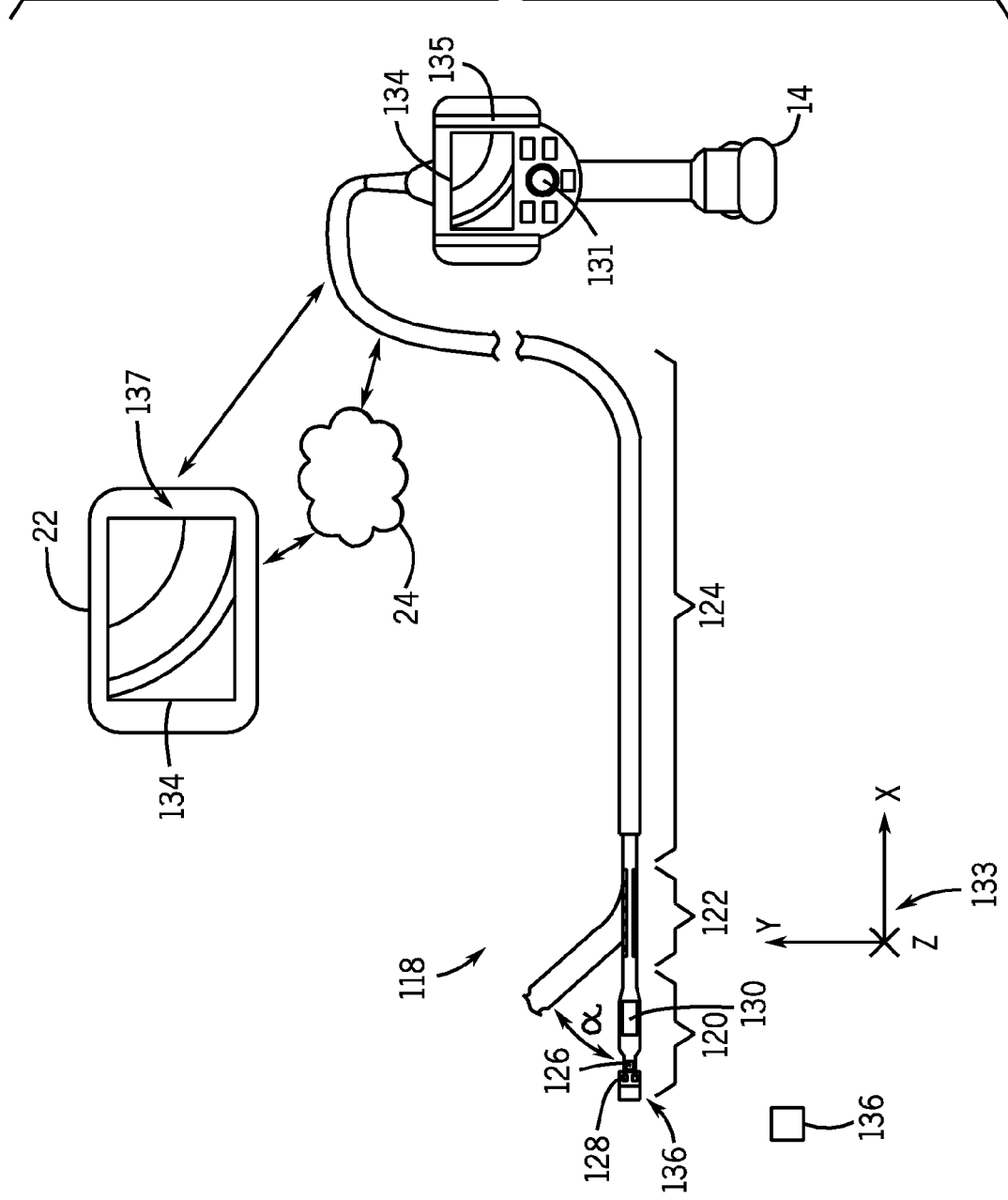
FIG. 3 is a front view illustrating an embodiment of a borescope system 14 communicatively coupled to the mobile device of FIG. 1 and a "cloud;"

FIG. 3 is a front view of the borescope 14 coupled to the mobile device 22 and the cloud 24. Accordingly, the borescope 14 may provide data to any number of devices connected to the cloud 24 or inside the cloud 24. As mentioned above, the mobile device 22 may be used to receive data from the borescope 14, to remote control the borescope 14, or a combination thereof. Indeed, the techniques described herein enable, for example, the communication of a variety of data from the borescope 14 to the mobile device 22, including but not limited to images, video, and sensor measurements, such as temperature, pressure, flow, clearance (e.g., measurement between a stationary component and a rotary component), and distance measurements. Likewise, the mobile device 22 may communicate control instructions, reprogramming instructions, configuration instructions, and the like, as described in more detail below.

As depicted the borescope 14, includes an insertion tube 118 suitable for insertion into a variety of location, such as inside of the turbomachinery 18, equipment 84, pipes or conduits 86, underwater locations 88, curves or bends 90, varies locations inside or outside of the aircraft system 104, the interior of pipe 108, and so on. The insertion tube 118 may include a head end section 120, an articulating section 122, and a conduit section 124. In the depicted embodiment, the head end section 120 may include a camera 126, one or more lights 128 (e.g., LEDs), and sensors 130. As mentioned above, the borescope's camera 126 may provide images and video suitable for inspection. The lights 128 may be used to provide for illumination when the head end 120 is disposed in locations having low light or no light.

During use, the articulating section 122 may be controlled, for example, by the mobile device 22 and/or a physical joy stick 131 disposed on the borescope 14. The articulating sections 122 may steer or "bend" in various dimensions. For example, the articulation section 122 may enable movement of the head end 120 in an X-Y plane X-Z plane and/or Y-Z plane of the depicted XYZ axes 133. Indeed, the physical joystick 131 and/or the mobile device 22 may both be used alone or in combination, to provide control actions suitable for disposing the head end 120 at a variety of angles, such as the depicted angle α. In this manner, the borescope head end 120 may be positioned to visually inspect desired locations. The camera 126 may then capture, for example, a video 134, which may be displayed in a screen 135 of the borescope 14 and a screen 137 of the mobile device 22, and may be recorded by the borescope 14 and/or the mobile device 22. In one embodiment, the screens 135 and 137 may be multi-touchscreens using capacitance techniques, resistive techniques, infrared grid techniques, and the like, to detect the touch of a stylus and/or one or more human fingers. Additionally or alternatively, images and the video 134 may be transmitted into the cloud 24.

Other data, including but not limited to sensor 130 data, may additionally be communicated and/or recorded by the borescope 14. The sensor 130 data may include temperature data, distance data, clearance data (e.g., distance between a rotating and a stationary component), flow data, and so on. In certain embodiments, the borescope 14 may include a plurality of replacement tips 136. For example, the replacement tips 136 may include retrieval tips such as snares, magnetic tips, gripper tips, and the like. The replacement tips 136 may additionally include cleaning and obstruction removal tools, such as wire brushes, wire cutters, and the like. The tips 136 may additionally include tips having differing optical characteristics, such as focal length, stereoscopic views, 3-dimensional (3D) phase views, shadow views, and so on. Additionally or alternatively, the head end 120 may include a removable and replaceable head end 120. Accordingly, a plurality of head ends 120 may be provided at a variety of diameters, and the insertion tube 118 maybe disposed in a number of locations having openings from approximately one millimeter to ten millimeters or more. Indeed, a wide variety of equipment and facilities may be inspected, and the data may be shared through the mobile device 22 and/or the cloud 24.

Figure 4:
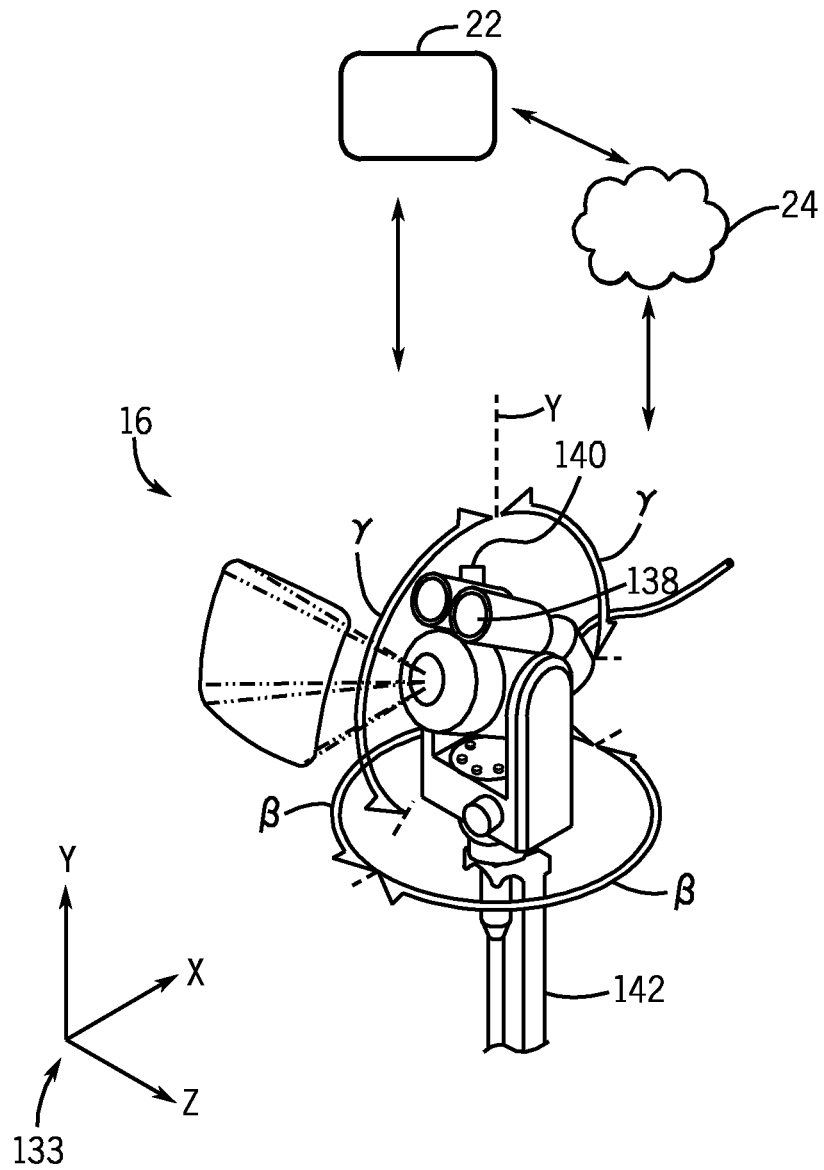
FIG. 4 is an illustration of an embodiment of a pan-tilt-zoom (PTZ) camera system communicatively coupled to the mobile device of FIG. 1.

FIG. 4 is a perspective view of an embodiment of the transportable PTZ camera 16 communicatively coupled to the mobile device 22 and to the cloud 24. As mentioned above, the mobile device 22 and/or the cloud 24 may remotely manipulate the PTZ camera 16 to position the PTZ camera 16 to view desired equipment and locations. In the depicted example, the PTZ camera 16 may be tilted and rotated about the Y-axis. For example, the PTZ camera 16 may be rotated at an angle β between approximately 0° to 180°, 0° to 270°, 0° to 360°, or more about the Y-axis. Likewise, the PTZ camera 16 may be tilted, for example, about the Y-X plane at an angle γ of approximately 0° to 100°, 0° to 120°, 0° to 150°, or more with respect to the Y-Axis. Lights 138 may be similarly controlled, for example, to active or deactivate, and to increase or decrease a level of illumination (e.g., lux) to a desired value. Sensors 140, such as a laser rangefinder, may also be mounted onto the PTZ camera 16, suitable for measuring distance to certain objects. Other sensors 140 may be used, including long-range temperature sensors (e.g., infrared temperature sensors), pressure sensors, flow sensors, clearance sensors, and so on.

The PTZ camera 16 may be transported to a desired location, for example, by using a shaft 142. The shaft 142 enables the camera operator 30 to move the camera and to position the camera, for example, inside of locations 86, 108, underwater 88, into hazardous (e.g., hazmat) locations, and so on. Additionally, the shaft 142 may be used to more permanently secure the PTZ camera 16 by mounting the shaft 142 onto a permanent or semi-permanent mount. In this manner, the PTZ camera 16 may be transported and/or secured at a desired location. The PTZ camera 16 may then transmit, for example by using wireless techniques, image data, video data, sensor 140 data, and the like, to the mobile device 22 and/or cloud 24. Accordingly, data received from the PTZ camera 16 may be remotely analyzed and used to determine the condition and suitability of operations for desired equipment and facilities. Indeed, the techniques described herein may provide for a comprehensive inspection and maintenance process suitable for planning, inspecting, analyzing, and/or sharing a variety of data by using the aforementioned devices 12, 14, 16, 22, 92, 94, 96, and the cloud 24, as described in more detail below with respect to FIG. 5.

Figure 5:
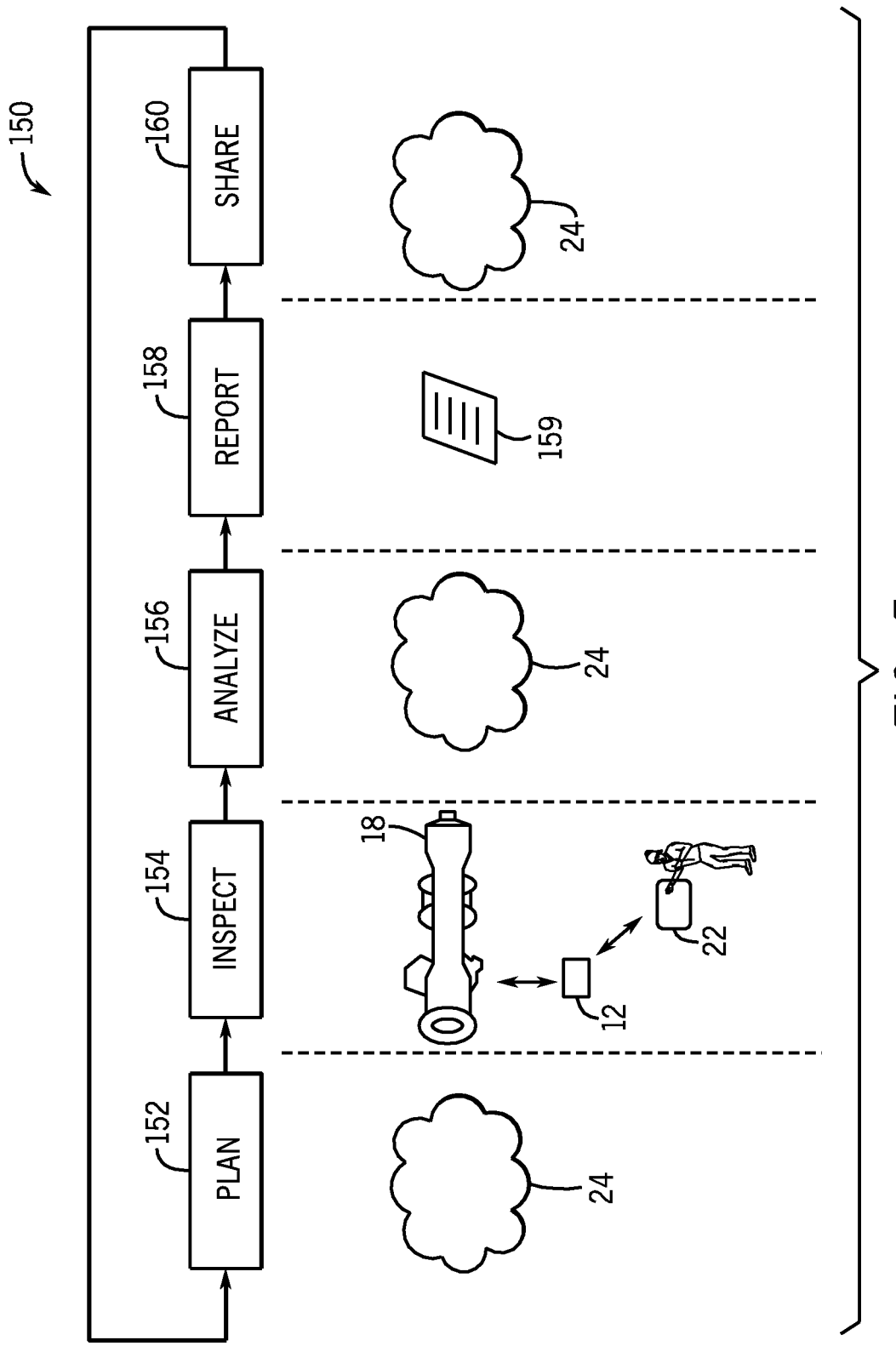
FIG. 5 is a flowchart illustrating an embodiment of a process useful in using the distributed NDT system for planning, inspecting, analyzing, reporting, and sharing of data, such as inspection data.

FIG. 5 is a flowchart of an embodiment of a process 150 suitable for planning, inspecting, analyzing, and/or sharing a variety of data by using the aforementioned devices 12, 14, 16, 22, 92, 94, 96, and the cloud 24. Indeed, the techniques described herein may use the devices 12, 14, 16, 22, 92, 94, 96 to enable processes, such as the depicted process 150, to more efficiently support and maintain a variety of equipment. In certain embodiments, the process 150 or portions of the process 150 may be included in non-transitory computer-readable media stored in memory, such as the memory 15, 19, 23, 93, 97, 101 and executable by one or more processors, such as the processors 17, 21, 25, 95, 99, 103.

In one example, the process 150 may plan (block 152) for inspection and maintenance activities. Data acquired by using the devices 12, 14, 16, 22, 42, 44, 46, an others, such as fleet data acquired from a fleet of turbomachinery 18, from equipment users (e.g., aircraft 104 service companies), and/or equipment manufacturers, may be used to plan (block 152) maintenance and inspection activities, more efficient inspection schedules for machinery, flag certain areas for a more detailed inspection, and so on. The process 150 may then enable the use of a single mode or a multi-modal inspection (block 154) of desired facilities and equipment (e.g., turbomachinery 18). As mentioned above, the inspection (block 154) may use any one or more of the NDT inspection devices 12 (e.g., borescope 14, PTZ camera 16, eddy current inspection device 92, ultrasonic flaw detector 94, digital radiography device 96), thus providing with one or more modes of inspection (e.g., visual, ultrasonic, eddy current, x-ray). In the depicted embodiment, the mobile device 22 may be used to remote control the NDT inspection devices 12, to analyze data communicated by the NDT inspection devices 12, to provide for additional functionality not included in the NDT inspection devices 12 as described in more detail herein, to record data from the NDT inspection devices 12, and to guide the inspection (block 154), for example, by using menu-driven inspection (MDI) techniques, among others.

Results of the inspection (block 154), may then be analyzed (block 156), for example, by using the NDT device 12, by transmitting inspection data to the cloud 24, by using the mobile device 22, or a combination thereof. The analysis may include engineering analysis useful in determining remaining life for the facilities and/or equipment, wear and tear, corrosion, erosion, and so forth. The analysis may additionally include operations research (OR) analysis used to provide for more efficient parts replacement schedules, maintenance schedules, equipment utilization schedules, personnel usage schedules, new inspection schedules, and so on. The analysis (block 156) may then be reported (block 158), resulting in one or more reports 159, including reports created in or by using the cloud 24, detailing the inspection and analysis performed and results obtained. The reports 159 may then be shared (block 160), for example, by using the cloud 24, the mobile device 22, and other techniques, such as workflow sharing techniques. In one embodiment, the process 150 may be iterative, thus, the process 150 may iterate back to planning (block 152) after the sharing (block 160) of the reports 159. By providing for embodiments useful in using the devices (e.g., 12, 14, 16, 22, 92, 94, 96) described herein to plan, inspect, analyze, report, and share data, the techniques described herein may enable a more efficient inspection and maintenance of the facilities 20, 106 and the equipment 18, 104. Indeed, the transfer of multiple categories of data may be provided, as described in more detail below with respect to FIG. 6.

Figure 6:
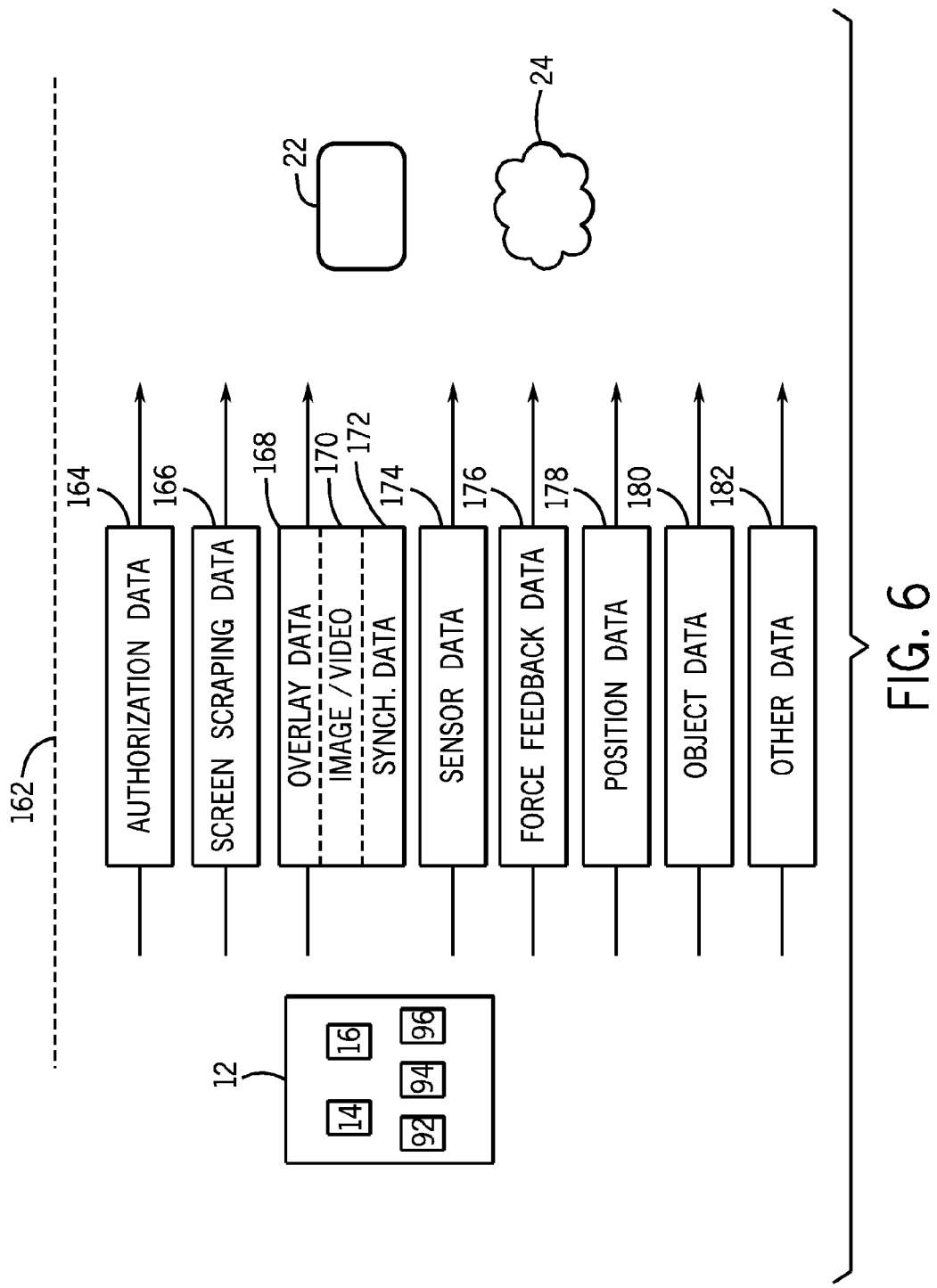
FIG. 6 is a block diagram of an embodiment of information flow through a wireless conduit.

FIG. 6 is a data flow diagram depicting an embodiment of the flow of various data categories originating from the NDT inspection devices 12 (e.g., devices 14, 16, 92, 94, 96) and transmitted to the mobile device 22 and/or the cloud 24. As mentioned above, the NDT inspection devices 12 may use a wireless conduit 162 to transmit the data. In one embodiment, the wireless conduit 112 may include WiFi (e.g., 802.11x), cellular conduits (e.g., HSPA, HSPA+, LTE, WiMax), NFC, Bluetooth, PANs, and the like. The wireless conduit 162 may use a variety of communication protocols, such as TCP/IP, UDP, SCTP, socket layers, and so on. In certain embodiments, the wireless conduit 162 may include secure layers, such as SSL, VPN layers, encrypted layers, challenge key authentication layers, token authentication layers, and so on. Accordingly, an authorization data 164 may be used to provide any number of authorization or login information suitable to pair or otherwise authenticate the NDT inspection device 12 to the mobile device 22 and/or the cloud 24. Additionally, the wireless conduit 162 may dynamically compress data, depending on, for example, currently available bandwidth and latency. The mobile device 22 may then uncompress and display the data. Compression/decompression techniques may include H.261, H.263, H.264, moving picture experts group (MPEG), MPEG-1, MPEG-2, MPEG-3, MPEG-4, DivX, and so on.

In certain modalities (e.g., visual modalities), images and video may be communicated by using certain of the NDT inspection devices 12. Other modalities may also send video, sensor data, and so on, related to or included in their respective screens. The NDT inspection device 12 may, in addition to capturing images, overlay certain data onto the image, resulting in a more informative view. For example, a borescope tip map may be overlaid on the video, showing an approximation of the disposition of a borescope tip during insertion so as to guide the operator 26 to more accurately position the borescope camera 126. The overlay tip map may include a grid having four quadrants, and the tip 136 disposition may be displayed as dot in any portion or position inside of the four quadrants. A variety of overlays may be provided, as described in more detail below, including measurement overlays, menu overlays, annotation overlays, and object identification overlays. The image and video data, such as the video 84, may then be displayed, with the overlays generally displayed on top of the image and video data.

In one embodiment, the overlays, image, and video data may be "screen scraped" from the screen 135 and communicated as screen scrapping data 166. The screen scrapping data 166 may then be displayed on the mobile device 22 and other display devices communicatively coupled to the cloud 24. Advantageously, the screen scrapping data 166 may be more easily displayed. Indeed, because pixels may include both the image or video and overlays in the same frame, the mobile device 22 may simply display the aforementioned pixels. However, providing the screen scraping data may merge both the images with the overlays, and it may be beneficial to separate the two (or more) data streams. For example, the separate data streams (e.g., image or video stream, overlay stream) may be transmitted approximately simultaneously, thus providing for faster data communications. Additionally, the data streams may be analyzed separately, thus improving data inspection and analysis.

Accordingly, in one embodiment, the image data and overlays may be separated into two or more data streams 168 and 170. The data stream 168 may include only overlays, while the data stream 170 may include images or video. In one embodiment, the images or video 170 may be synchronized with the overlays 168 by using a synchronization signal 172. For example, the synchronization signal may include timing data suitable to match a frame of the data stream 170 with one or more data items included in the overlay stream 168. In yet another embodiment, no synchronization data 172 data may be used. Instead, each frame or image 170 may include a unique ID, and this unique ID may be matched to one or more of the overlay data 168 and used to display the overlay data 168 and the image data 170 together.

The overlay data 168 may include a tip map overlay. For example, a grid having four squares (e.g., quadrant grid) may be displayed, along with a dot or circle representing a tip 136 position. This tip map may thus represent how the tip 136 is being inserted inside of an object. A first quadrant (top right) may represent the tip 136 being inserted into a top right corner looking down axially into the object, a second quadrant (top left) may represent the tip 136 being inserted into a left right corner looking down axially, a third quadrant (bottom left) may represent the tip 136 being inserted into a bottom left corner, and a fourth quadrant (bottom right) may represent the tip 136 being inserted into a bottom right corner. Accordingly, the borescope operator 26 may more easily guide insertion of the tip 136.

The overlay data 168 may also include measurement overlays. For example, measurement such as length, point to line, depth, area, multi-segment line, distance, skew, and circle gauge may be provided by enabling the user to overlay one or more cursor crosses (e.g., "+") on top of an image. In one embodiment a stereo probe measurement tip 136, or a shadow probe measurement tip 136 may be provided, suitable for measurements inside of objects, including stereoscopic measurements and/or by projecting a shadow onto an object. By placing a plurality of cursor icons (e.g., cursor crosses) over an image, the measurements may be derived using stereoscopic techniques. For example, placing two cursors icons may provide for a linear point-to-point measurement (e.g., length). Placing three cursor icons may provide for a perpendicular distance from a point to a line (e.g., point to line). Placing four cursor icons may provide for a perpendicular distance between a surface (derived by using three cursors) and a point (the fourth cursor) above or below the surface (e.g., depth). Placing three or more cursors around a feature or defect may then give an approximate area of the surface contained inside the cursors. Placing three or more cursors may also enable a length of a multi-segment line following each cursor.

Likewise, by projecting a shadow, the measurements may be derived based on illumination and resulting shadows. Accordingly, by positioning the shadow across the measurement area, then placing two cursors as close as possible to the shadow at furthermost points of a desired measurement may result in the derivation of the distance between the points. Placing the shadow across the measurement area, and then placing cursors at edges (e.g., illuminated edges) of the desired measurement area approximately to the center of a horizontal shadow may result in a skew measurement, otherwise defined as a linear (point-to-point) measurement on a surface that is not perpendicular to the probe 14 view. This may be useful when a vertical shadow is not obtainable.

Similarly, positioning a shadow across the measurement area, and then placing one cursor on a raised surface and a second cursor on a recessed surface may result in the derivation of depth, or a distance between a surface and a point above or below the surface. Positioning the shadow near the measurement area, and then placing a circle (e.g., circle cursor of user selectable diameter, also referred to as circle gauge) close to the shadow and over a defect may then derive the approximate diameter, circumference, and/or area of the defect.

Overlay data 168 may also include annotation data. For example, text and graphics (e.g. arrow pointers, crosses, geometric shapes) may be overlaid on top of an image to annotate certain features, such as "surface crack." Additionally, audio may be captured by the NDT inspection device 12, and provided as an audio overlay. For example, a voice annotation, sounds of the equipment undergoing inspection, and so on, may be overlaid on an image or video as audio. The overlay data 168 received by the mobile device 22 and/or cloud 24 may then be rendered by a variety of techniques. For example, HTML5 or other markup languages may be used to display the overlay data 168. In one embodiment, the mobile device 22 and/or cloud 24 may provide for a first user interface different from a second user interface provided by the NDT device 12. Accordingly, the overlay data 168 may be simplified and only send basic information. For example, in the case of the tip map, the overlay data 168 may simply include X and Y data correlative to the location of the tip, and the first user interface may then use the X and Y data to visually display the tip on a grid.

Additionally sensor data 174 may be communicated. For example, data from the sensors 126, 140, and x-ray sensor data, eddy current sensor data, and the like may be communicated. In certain embodiments, the sensor data 174 may be synchronized with the overlay data 168, for example, overlay tip maps may be displayed alongside with temperature information, pressure information, flow information, clearance, and so on. Likewise, the sensor data 174 may be displayed alongside the image or video data 170.

In certain embodiments, force feedback or haptic feedback data 176 may be communicated. The force feedback data 176 may include, for example, data related to the borescope 14 tip 136 abutting or contacting against a structure, vibrations felt by the tip 136 or vibration sensors 126, force related to flows, temperatures, clearances, pressures, and the like. The mobile device 22 may include, for example, a tactile layer having fluid-filled microchannels, which, based on the force feedback data 176, may alter fluid pressure and/or redirect fluid in response. Indeed, the techniques describe herein, may provide for responses actuated by the mobile device 22 suitable for representing sensor data 174 and other data in the conduit 162 as tactile forces.

The NDT devices 12 may additionally communicate position data 178. For example, the position data 178 may include locations of the NDT devices 12 in relation to equipment 18, 104, and/or facilities 20, 106. For example, techniques such as indoor GPS, RFID, triangulation (e.g., WiFi triangulation, radio triangulation) may be used to determine the position 178 of the devices 12. Object data 180 may include data related to the object under inspection. For example, the object data 180 may include identifying information (e.g., serial numbers), observations on equipment condition, annotations (textual annotations, voice annotations), and so on. Other types of data 182 may be used, including but not limited to menu-driven inspection data, which when used, provides a set of pre-defined "tags" that can be applied as text annotations and metadata. These tags may include location information (e.g., $1^{st}$ stage HP compressor) or indications (e.g., foreign object damage) related to the object undergoing inspection. Other data 182 may additionally include remote file system data, in which the mobile device 22 may view and manipulate files and file constructs (e.g., folders, subfolders) of data located in the memory 25 of the NDT inspection device 12. Accordingly, files may be transferred to the mobile device 22 and cloud 24, edited and transferred back into the memory 25. By communicating the data 164-182 to the mobile device 22 and the cloud 24, the techniques described herein may enable a faster and more efficient process 150.

Graphical Filter for Inspection Data

Figure 7:
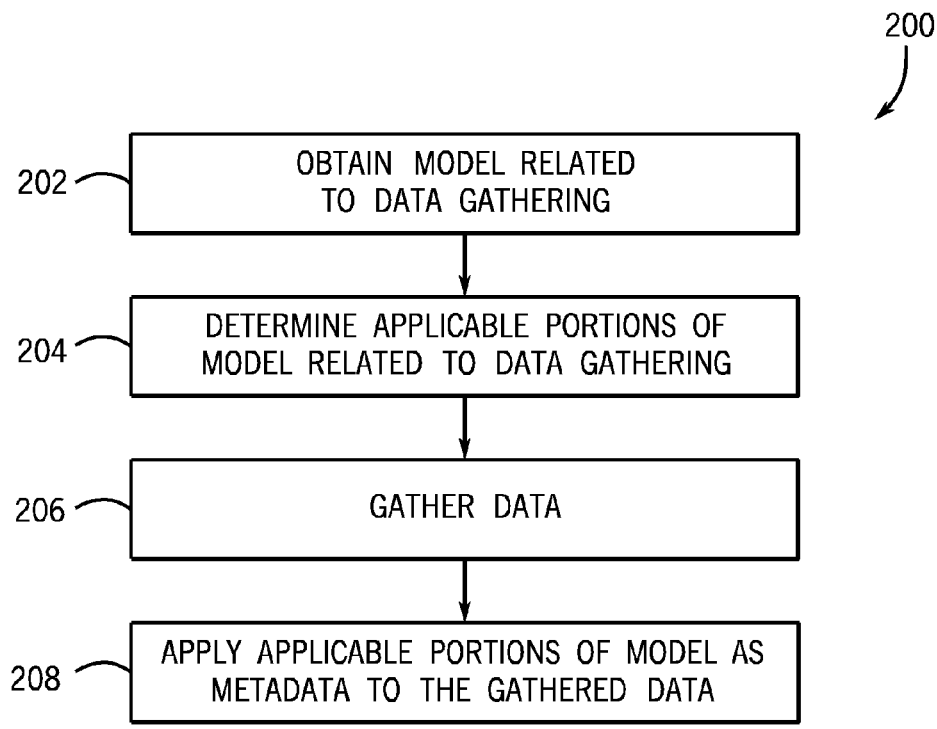
FIG. 7 is a flowchart depicting a process for applying graphical filter data to gathered inspection data, in accordance with an embodiment.

As previously discussed, it may be beneficial to provide inspection data using a graphical filter. The graphical filter may provide more efficient access to particular inspection data by enabling an inspector or other personnel to easily filter particular data. Graphical filter data may be bound to the inspection data, such that it may be later accessed using the graphical filter. FIG. 7 is a flowchart depicting a process 200 for applying graphical filter data to gathered inspection data, in accordance with an embodiment. The process 200 may begin by obtaining a model related to the object being inspected (block 202). For example, as described herein, the inspection instrument (e.g., the NDT inspection device 12 or mobile device 22) or other computing device may be aware of a particular object that is being inspected. Accordingly, the inspection instrument may obtain a 2D or 3D model of the product being inspected. For example, if the inspection instrument knows that the current inspection relates to a particular aircraft, a model of the aircraft may be downloaded to the inspection instrument. In some embodiments, the actual model is not downloaded, but instead location indicators (e.g., part identifier labels, coordinates, etc.) may be obtained by the inspection instrument.

Once the model and/or location indicators are obtained, the portions of the model and/or location indicators applicable to the particular inspection are determined (block 204). For example, if the inspection is on at or around the cockpit of the aircraft 54, the determined portion of the model may include the cockpit and/or the determined coordinates or other location indicator may similarly identify the cockpit. Many layers of location indicators may be determined at this step. For example, when inspecting the wings of the aircraft 54, any granularity of location indication may be obtained. In some embodiments, the system may determine a very granular understanding of the applicable portions of the model and/or location indicators. For example, the applicable portion may be determined to be a particular flap of the left wing. In alternative embodiments, a less granular determination may be made. For example, the applicable portions may simply denote the aircraft 54 wings.

The inspection data is gathered as described herein (block 206) and the determined applicable portions and/or location indicators are applied as metadata to the gathered data (block 208). For example, borescope image data may be obtained and an indication of the applicable portion of the model where the image data was obtained may be appended as an attribute to the image data. Accordingly, graphical filter data of the model is now attributed to the image data, which, as will be discussed in more detail below, is useful for graphically filtering the data. The application of the metadata to the gathered data may take place using any method of creating a relationship between the metadata and the gathered data. For example, in some embodiments, a relational database may create relationships between the metadata and the gathered data. In alternative embodiments, attributes may be set in the file system, defining the metadata as an attribute for a particular gathered data file. Other databases may be used, including cloud-based databases, such as virtual machine image (VMI) databases, and/or database as a service systems.

Figure 8:
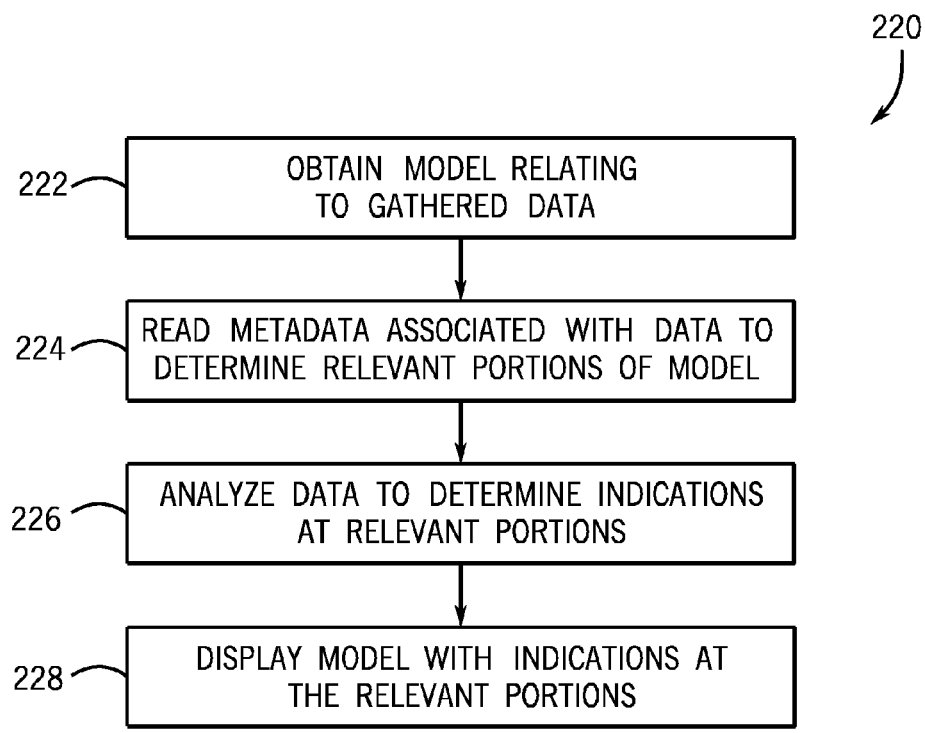
FIG. 8 is a flowchart depicting a process for presenting inspection data using a graphical filter, in accordance with an embodiment.

Once the graphical filter data is applied to the inspection data, it may be used to graphically present the data. FIG. 8 is a flowchart depicting a process 220 for presenting inspection data using the graphical filter data, in accordance with an embodiment. The process 220 begins by obtaining a 2D or 3D model of the object inspected (block 222). For example, if the inspection data relates to a Boeing 777, a 2D or 3D model of the Boeing 777 is obtained. In alternative embodiments, a more simplistic and generalized model may be obtained. For example, a generic aircraft model may be obtained. As previously discussed, metadata defining the applicable portions of the model and/or other location indicators may be attributed to the inspection data. The metadata is read (block 224) and analyzed (block 226) to determine the relevant portions of the model associated with the particular inspection data. As previously mentioned, a generalized model may be used. In embodiments where a generalized model is used and/or the model obtained for presentation of inspection data does not match the model used to apply the metadata to the gathered inspection data, a conversion of the metadata may occur. For example, if the metadata was obtained using a granular model and the presentation model is less granular, the system may convert the metadata to a form understandable by the presentation model. Thus, if the metadata provided that the applicable location was a particular left wing flap, but the presentation model did not differentiate flaps from other parts of the wing, the system could convert the flap metadata to a less granular portion (e.g., the left wing or the wings of the aircraft). Once the relevant portions of the presentation model applicable to the inspection data are determined, the presentation model may be displayed with an indication at the relevant portions (block 228), indicating that inspection data for that portion is available.

Figure 9:
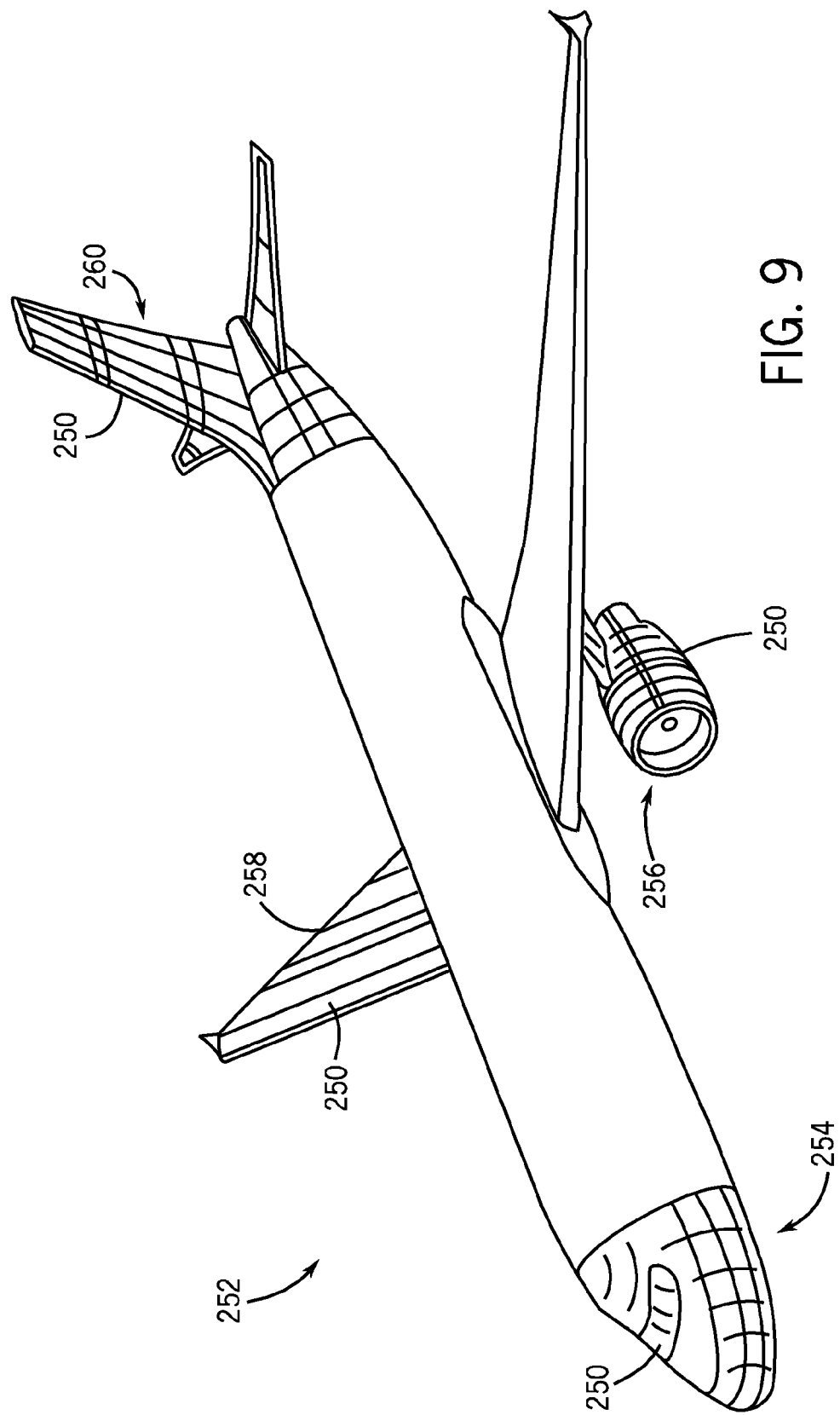
FIG. 9 is an example of providing inspection characteristics and data using a wire frame, in accordance with an embodiment.

FIG. 9 is an example of providing inspection characteristics and data using a wire frame 250 on a presentation model 252, in accordance with an embodiment. For example, using the process 220 described above, the presentation model 252 may be displayed with wire frame 250 indicators. These 250 indicators provide an indication that inspection information for particular components of the object are available. For example, the wire frame 250 surrounds the cockpit 254, the left turbine engine 256, the right wing 258, and the tail 260, indicating that inspection information for each of these portions of the aircraft are available.

As may be appreciated, the wire frame 250 indicators may be very helpful in providing an indication of particular portions of an object that have been inspected. These indicators may be useful to understand overall inspection progress by illustrating portions of the aircraft that have not yet been inspected. In some embodiments, the wire frame 250 indicators may be provided only when the inspection data is not stale (e.g., is within a certain threshold time period). Thus, in these embodiments, the wire frame 250 may provide indication of portions where current (e.g., non-stale) inspection data exists, thus providing a better understanding of portions of the object that need additional inspection.

Figure 10:
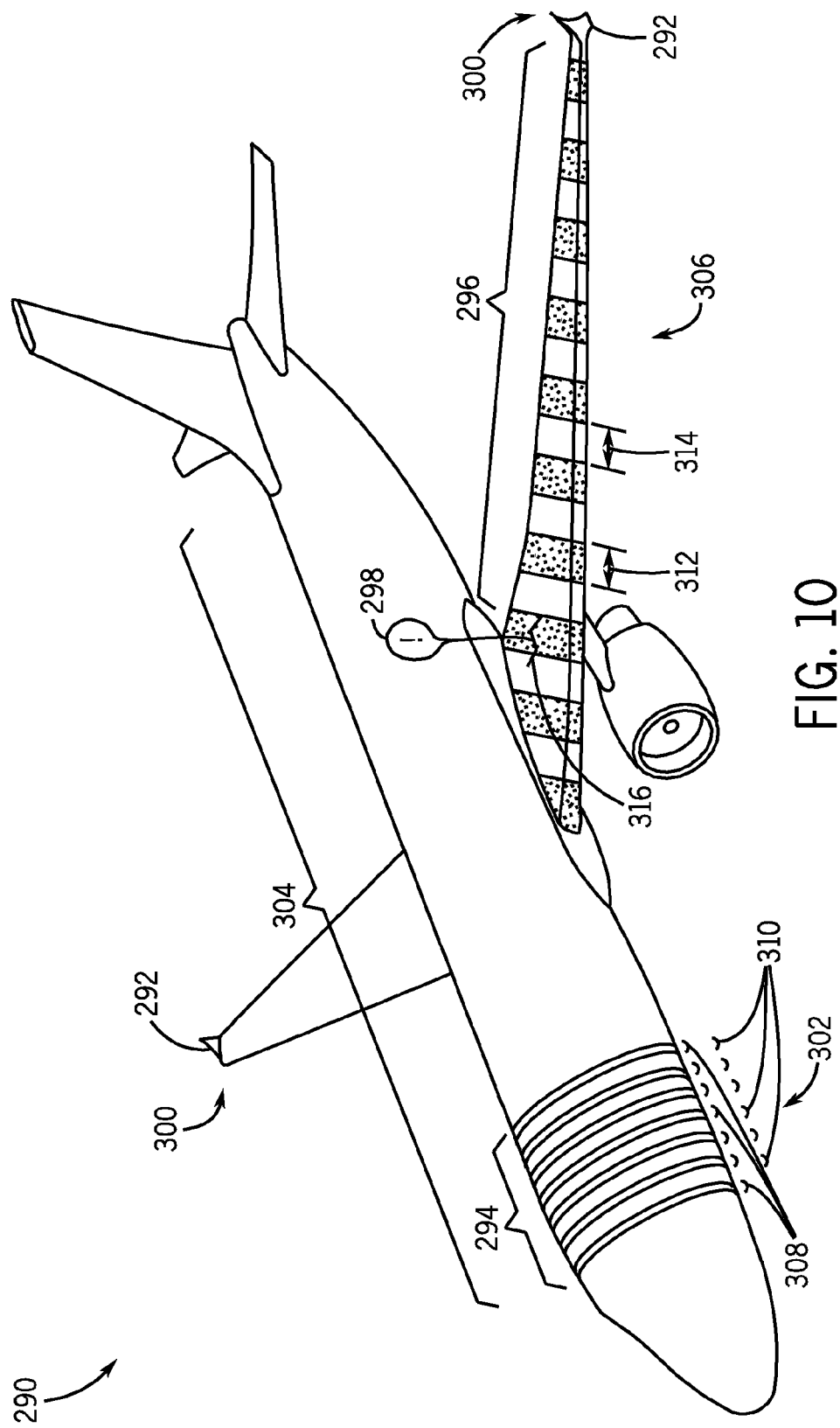
FIG. 10 is an example of providing inspection characteristics and data using variable-spaced wire frames and inspection indicator icons, in accordance with an embodiment.

In some cases it may be beneficial to provide an indication of whether or not any inspection data exists, regardless of the characteristics of the inspection data (e.g., whether the inspection data is stale), in conjunction with an indication of portions that have stale data (or other characteristic of the data). FIG. 10 is an example of providing an indication of portions of an object with inspection data and inspection data characteristic. The model 290 uses variable wire frames 292, 294 and 296 and inspection indicator icons 298 to provide inspection data indications, in accordance with an embodiment. Presence of the variable wire frames 292, 294, and 296 may indicate that inspection data exists for particular portions of the object. For instance, in the provided example, wire frame 292 may indicate that inspection data is available for the wing tips 300. Further, the wire frame 294 may indicate that inspection data exists for a forward portion 302 of the fuselage 304. The wire frame 296 may indicate that the left wing 306 has inspection data available.

Variable wire frames and/or indication icons may be used to provide additional indications regarding the available inspection data. For example, as may be appreciated, wire frames 292, 294, and 296 are all variably spaced with wires of a different thickness. For example, the wire frame 292 includes very tightly spaced wires with very thick wires. The wire frame 294 includes thin wires (as indicated by the thickness 308) and are spaced with a relatively moderate spacing 310. Additionally, the wire frame 296 includes wires with a relatively thick thickness 312 and relatively loose (e.g., wide) spacing 314.

The wire thickness and wire spacing may be used to present attributes of the inspection data. For example, in some embodiments, wire thickness may represent an amount of inspection data that is available and the wire spacing may indicate whether the data is fresh or stale. For example, the wire frame 292 may indicate that the inspection of the wing tips 300 is recent or "fresh" and that a significant amount of inspection data is available, because the wire frame 292 is very tightly spaced using very thick wires. The wire frame 294 may indicate that there is relatively little inspection data available for the forward portion 302 of the fuselage 304 based upon the wire thickness 308 and that the available inspection data is moderately recent based upon the wire spacing 310. Further, the wire frame 296 may indicate that there is a large amount of inspection data for the left wing 306, based upon the wire thickness 312, but that the inspection data is relatively stale, based upon the wire spacing 314.

In addition to wire frame indicators, indicator icons, such as indicator icon 298 may be used to indicate particular characteristics of inspection data. For example, the indicator icon 298 may indicate an anomaly and/or warnings for specific inspection data that is believed to be important (e.g., inspection data that indicates the breach of a particular safety standard, etc.). As indicated by the "!" label, the indicator icon 298 is intended to alert inspectors or other personnel of important inspection data. For example, a crack 316 may be present in the left wing 114, causing the inspection data to breach a safety standard. Upon analysis of the data, the system may determine this breach and provide the indicator icon 298 as an indication of the breach. Because applicable portions of the model are attributed in the inspection data, the indicator icon 298 may be presented in an approximate location where the breach was detected.

As may be appreciated, quite a bit of inspection data and/or inspection data characteristics may be obtained by quickly glancing at the presentation model with wire frame indicators. Though the preceding discussion has revolved around specific examples of indications based upon wire thickness and spacing, the intention is not to limit the wire frame variables that may provide particular indications or the particular characteristics of the inspection data that are presented based upon the variables in the wire frame. Further, the indicators are not limited to wire frame and icon indicators. Any variance to the presentation model may be used to provide an indication of the presence of inspection data for a particular portion of an object and/or particular characteristics of the inspection data.

Figure 11:
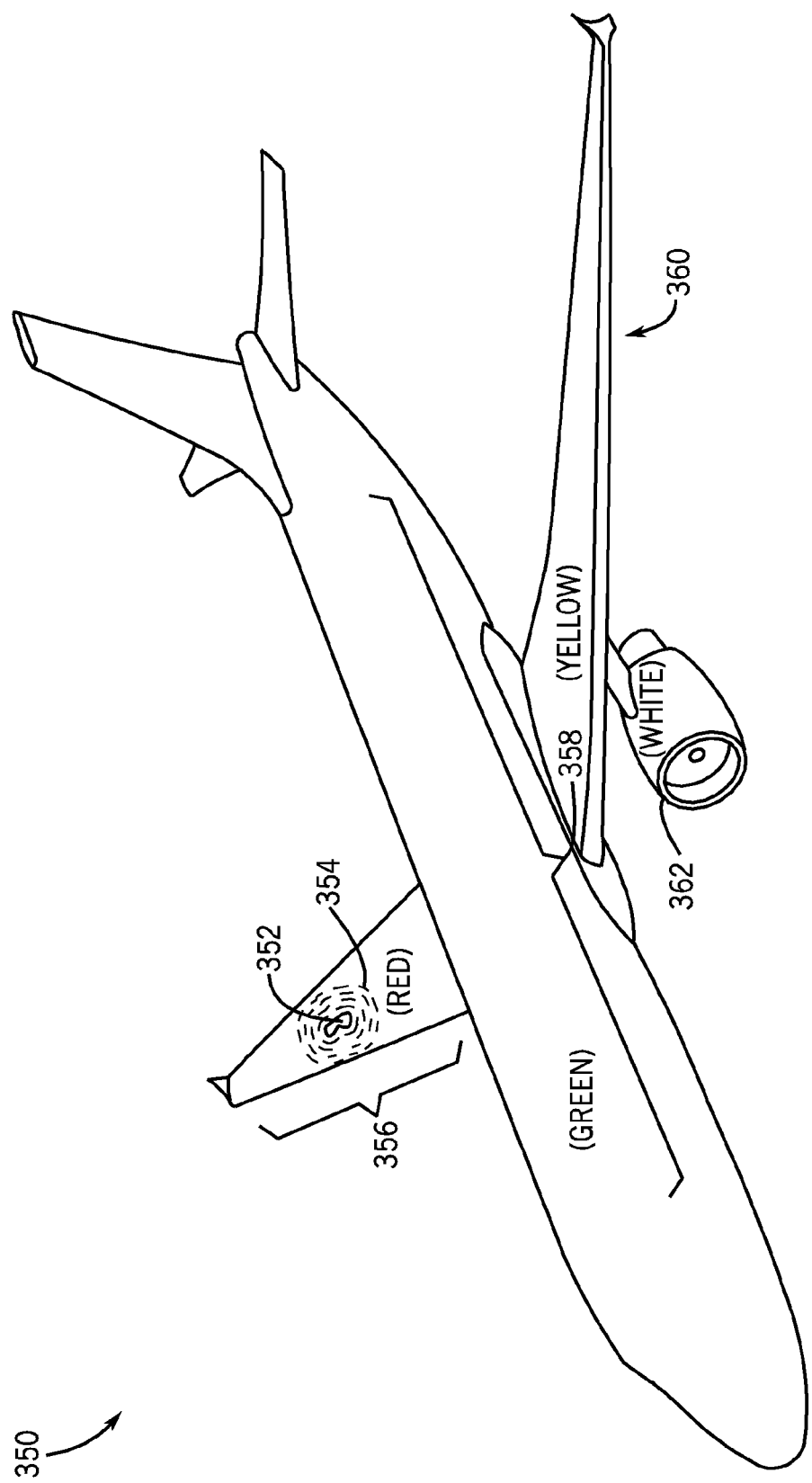
FIG. 11 is an example of providing inspection characteristics and data using colors and heat maps, in accordance with an embodiment.

For example, colors and/or color mappings may be added to the presentation model to illustrate characteristics of the inspection data. FIG. 11 illustrates an example of providing inspection characteristics and data using colors and color variation maps, in accordance with an embodiment. In the current embodiment, colors are added to the displayed model 350 to illustrate the criticality of the current inspection data known to the system. For example, red may represent that there are critical items that should be addressed, based upon the inspection data. Yellow may be used to indicate that inspection data that is either missing or showing a trend towards criticality and green may indicate that there are no inspection issue (e.g., the inspections are up to date and no critical or trending to critical issues have been detected). Further, in the current embodiment, white may represent that no inspection data exists for a particular component. In the current example of FIG. 11, assume a crack 352 exists. Accordingly, the inspection data may detect abnormalities (e.g., surface cracking, buckling, etc.). A color variation map 354 may provide varying shades of red, indicating a pinpointed area where the anomalies are rooted. Further, the entire wing 356 may be some shade of red, indicating a critical issue with the wing.

In the current example, the fuselage 358 is shaded green, indicating that inspection data is fresh and that no anomalies and/or trending towards critical issues exist. The left wing 360 is shaded yellow, indicating a trend pattern towards criticality and/or insufficient "fresh" inspection data. Further, the left turbine engine 362 is shaded white, indicating that no inspection data is available for that particular component. As previously mentioned, the provided examples discussed herein are not intended to limit the scope of the current specification. Any colors and/or color patterns could be used to provide additional indications of any number of characteristics of the inspection data.

Figure 12:
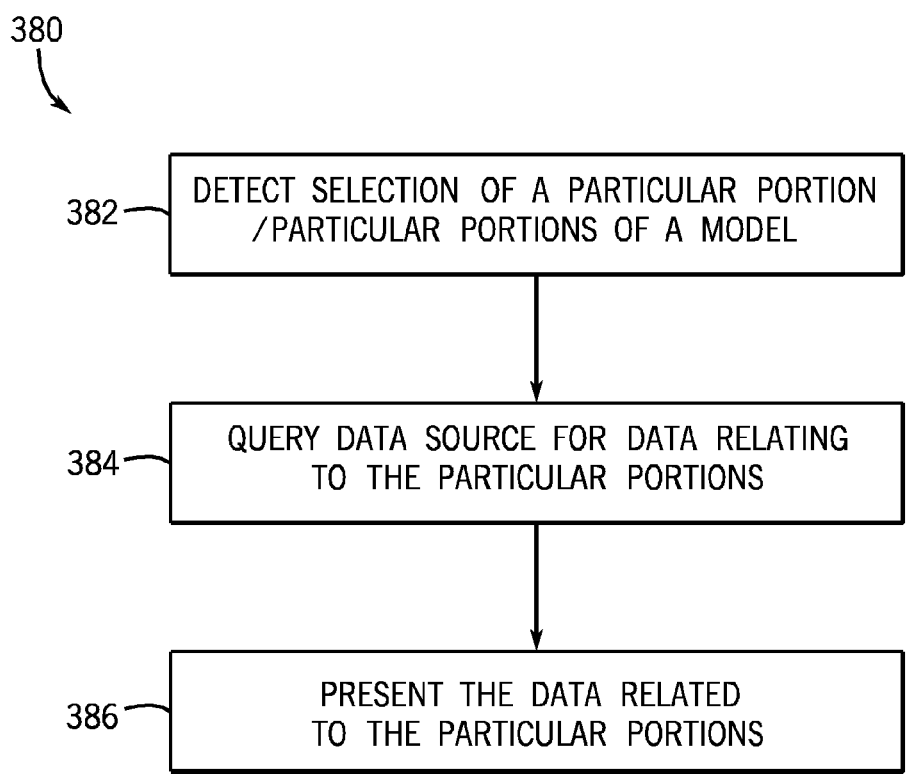
FIG. 12 is a flowchart illustrating a process for obtaining inspection data based upon a particular graphical filter element selection, in accordance with an embodiment.

Once an inspector or other personnel has been apprised of the inspection characteristics, the inspector or other personnel may desire to access particular inspection data. FIG. 12 is a flowchart illustrating a process 380 for obtaining inspection data based upon a particular graphical filter element selection, in accordance with an embodiment. The system may detect the selection of a particular portion or portions of the presentation model described above (block 382). For example, the inspector or other personnel may select a particular portion of the presentation model, by touching the portion on a touch screen displaying the presentation model or via a mouse click on a computer displaying the presentation model. Next, based upon the selections, a data source with access to the inspection data is queried (block 384). The data source may return the relevant inspection data related to the selections (block 386).

FIGS. 13-18 illustrate particular selections and the presentation of inspection data related to these selections. For example, in FIG. 13, as indicated by the pointer 402, the inspector has selected the fuselage graphical filter element 406 from the presentation model 400, indicating a desire to obtain specific inspection data regarding the fuselage 404. Based upon the selection, the system may query a data source (e.g., a local or cloud-computing database) having access to the inspection data. Because the inspection data is bound with relevant portions of the model, querying the data source with an indication of particular relevant portions results in graphically filtering the inspection data. For example, in the current example, the data source is queried based upon the fuselage of a particular aircraft. The data source returns the inspection data specific to the fuselage of that aircraft.

Figure 13:
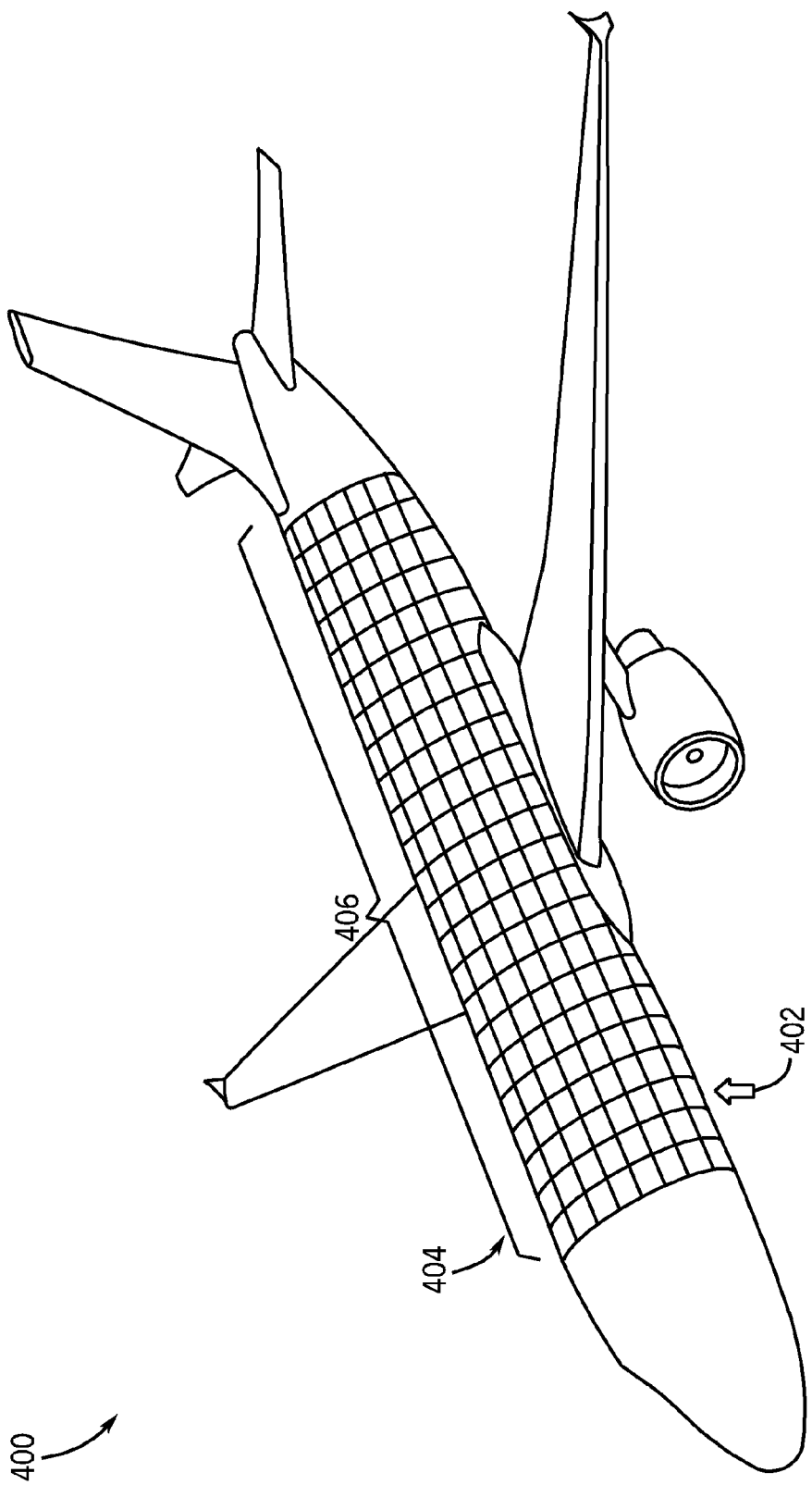
FIG. 13 is an example of selecting a fuselage graphical filter element to obtain specific inspection data, in accordance with an embodiment.
Figure 14:
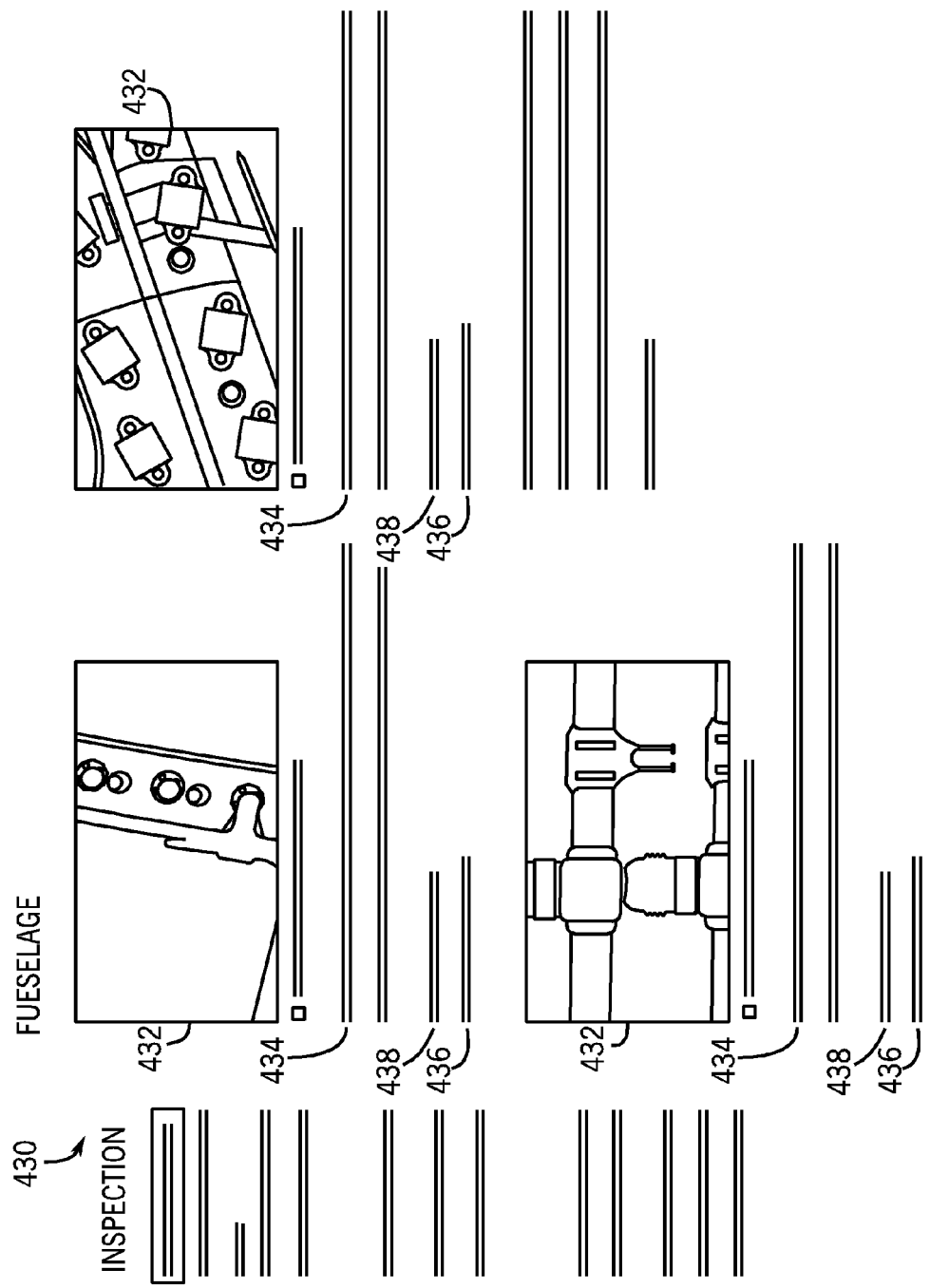
FIG. 14 is an example of filtered data obtained based upon the selection of FIG. 13, in accordance with an embodiment.

FIG. 14 is an example of filtered fuselage data obtained based upon the selection of FIG. 13, in accordance with an embodiment. As illustrated, an inspection report 430 is provided, displaying only data related to the selection provided by the operator (e.g., in this example the fuselage of the particular aircraft). The inspection report may include, for example, images 432, notes 434, inspection dates 436, names 438 of the inspector(s) completing the inspection, and any other pertinent inspection data.

The presentation of the inspection data may be configured in the system presenting the inspection. For example, configuration settings of the presentation system may enable an operator to be presented with data in a certain time range, data that is "fresh", or inspection data conforming to any other characteristic.

Figure 15:
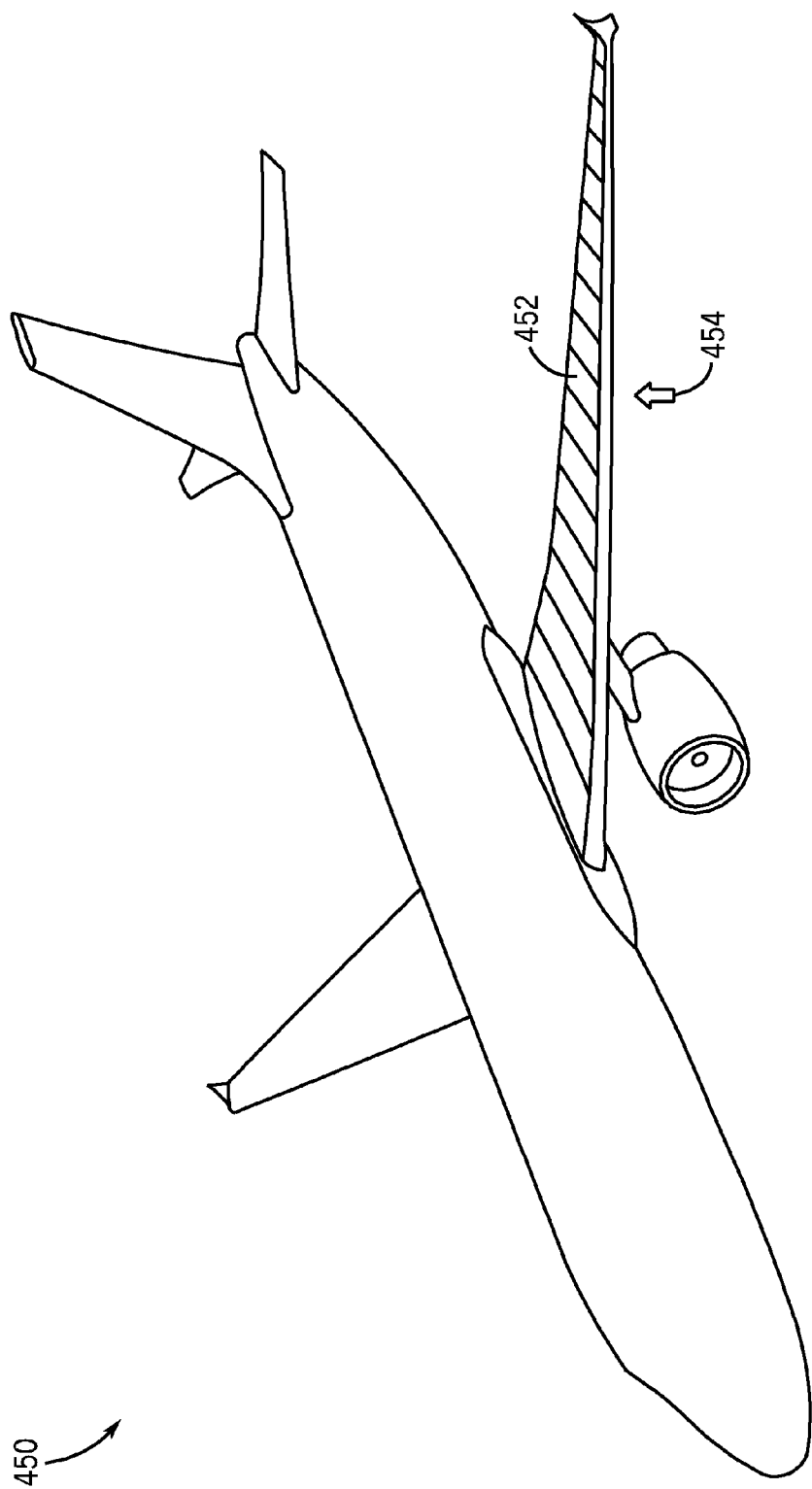
FIG. 15 is an example of selecting a wing graphical filter element to obtain specific inspection data, in accordance with an embodiment.
Figure 16:
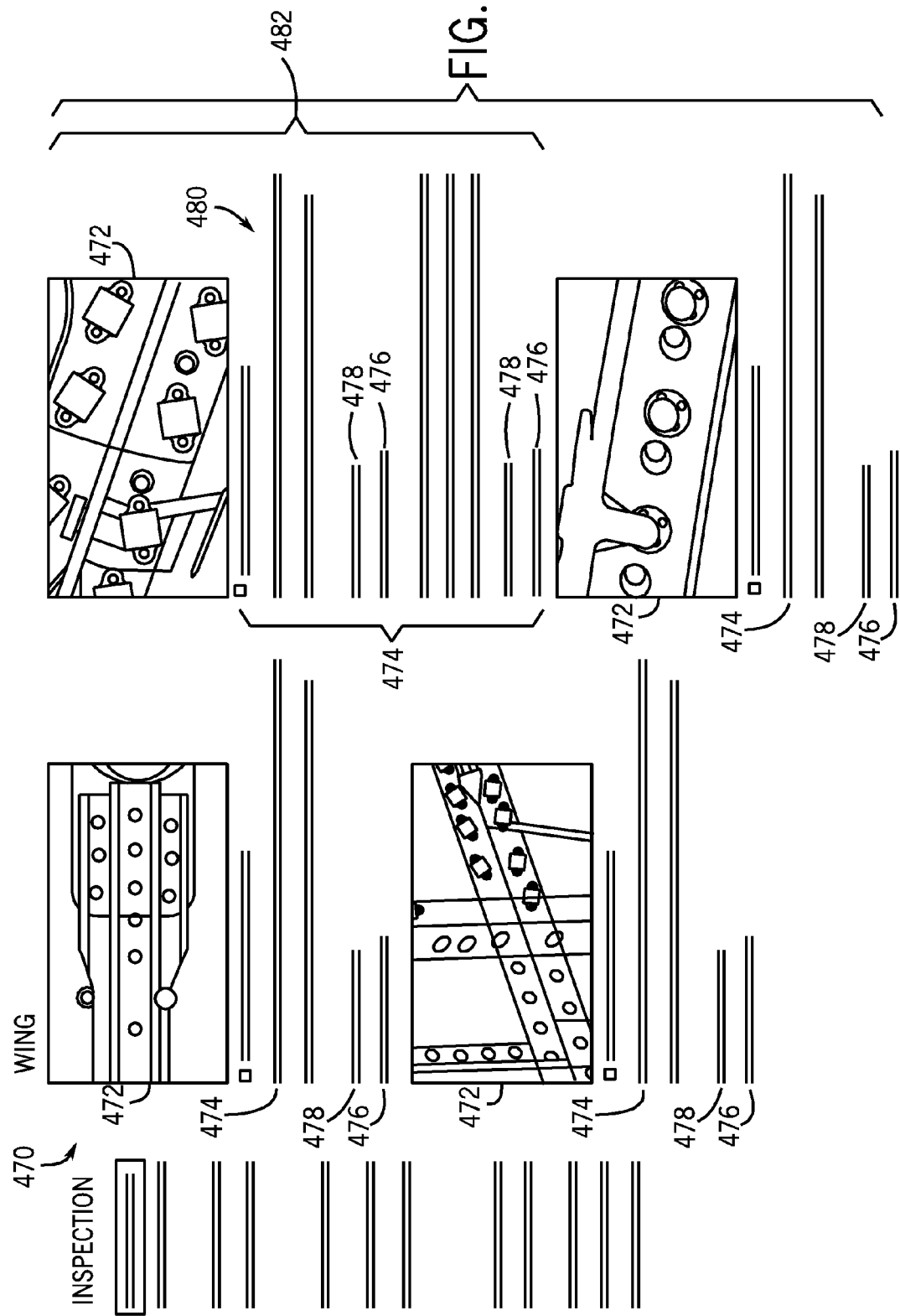
FIG. 16 is an example of filtered data obtained based upon the selection of FIG. 14, in accordance with an embodiment.

FIG. 15 is an example of an inspector or other personnel selecting a wing graphical filter element 452 of the model 450 to obtain specific inspection data, as indicated by the pointer 454. As discussed above, upon detecting the selection, the system queries the data source for inspection data relating to the selected wing. Accordingly, wing inspection data is retrieved by the system and a wing inspection report 470 is presented to the inspector, as illustrated in FIG. 16. Once again, only data related to the wing is provided to the inspector, because the wing was the only selection made by the inspector. Further, as above, the inspection report includes, for example, images 472, notes 474, inspection dates 476, names 478 of the inspector(s) completing the inspection, and any other pertinent inspection data. Further, as indicated by inspection data "ID 0005" 480 multiple sets of inspection data may be combined for a particular subcomponent. In the current example, Rich McCulley and Edward Turner provided individual notes for the "ID 0005" inspection. Their notes have been combined and presented to the user in a single container 482.

Figure 17:
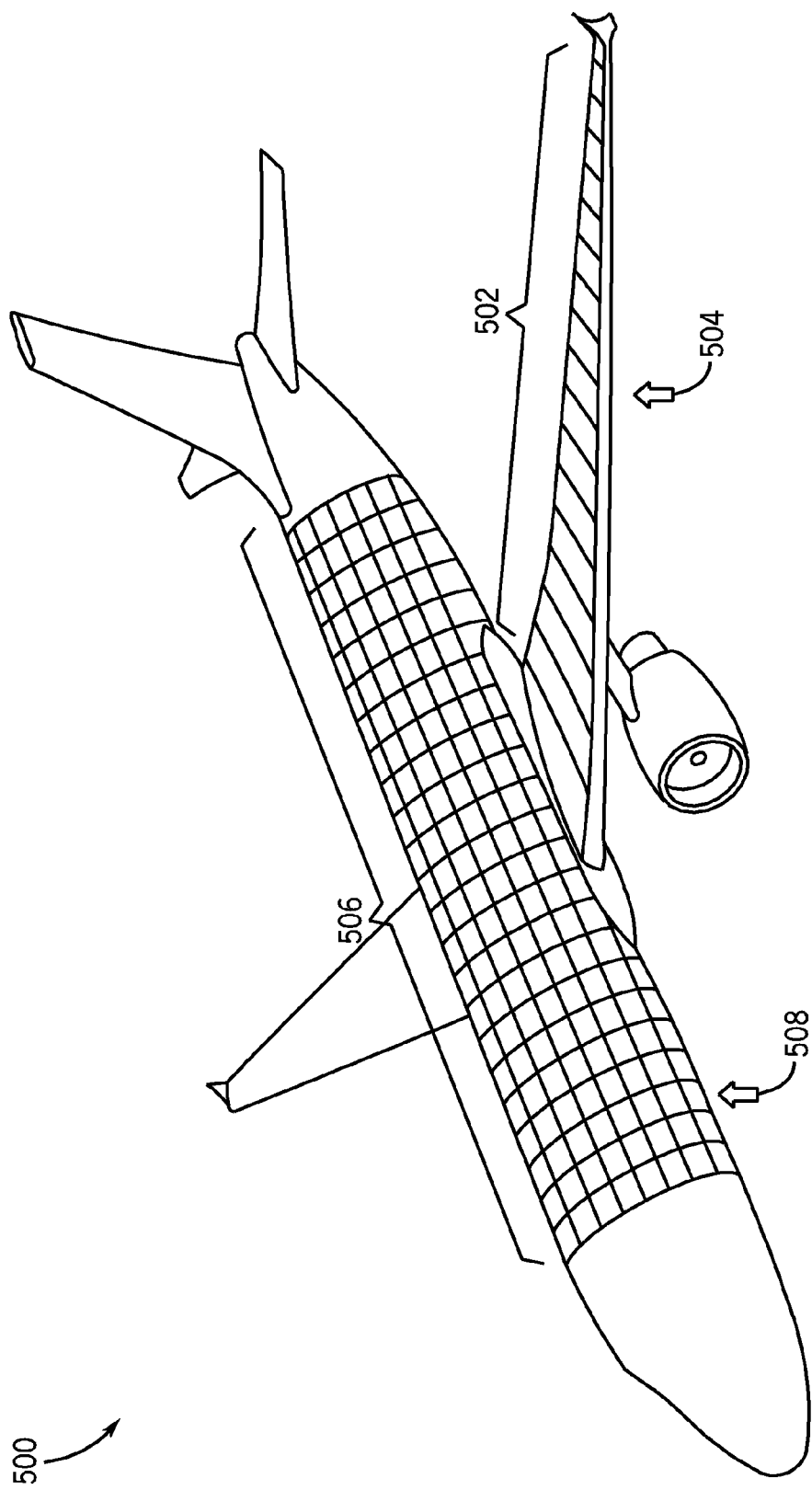
FIG. 17 is an example of selecting both graphical filter elements of FIGS. 13 and 14 to obtain specific inspection data, in accordance with an embodiment.
Figure 18:
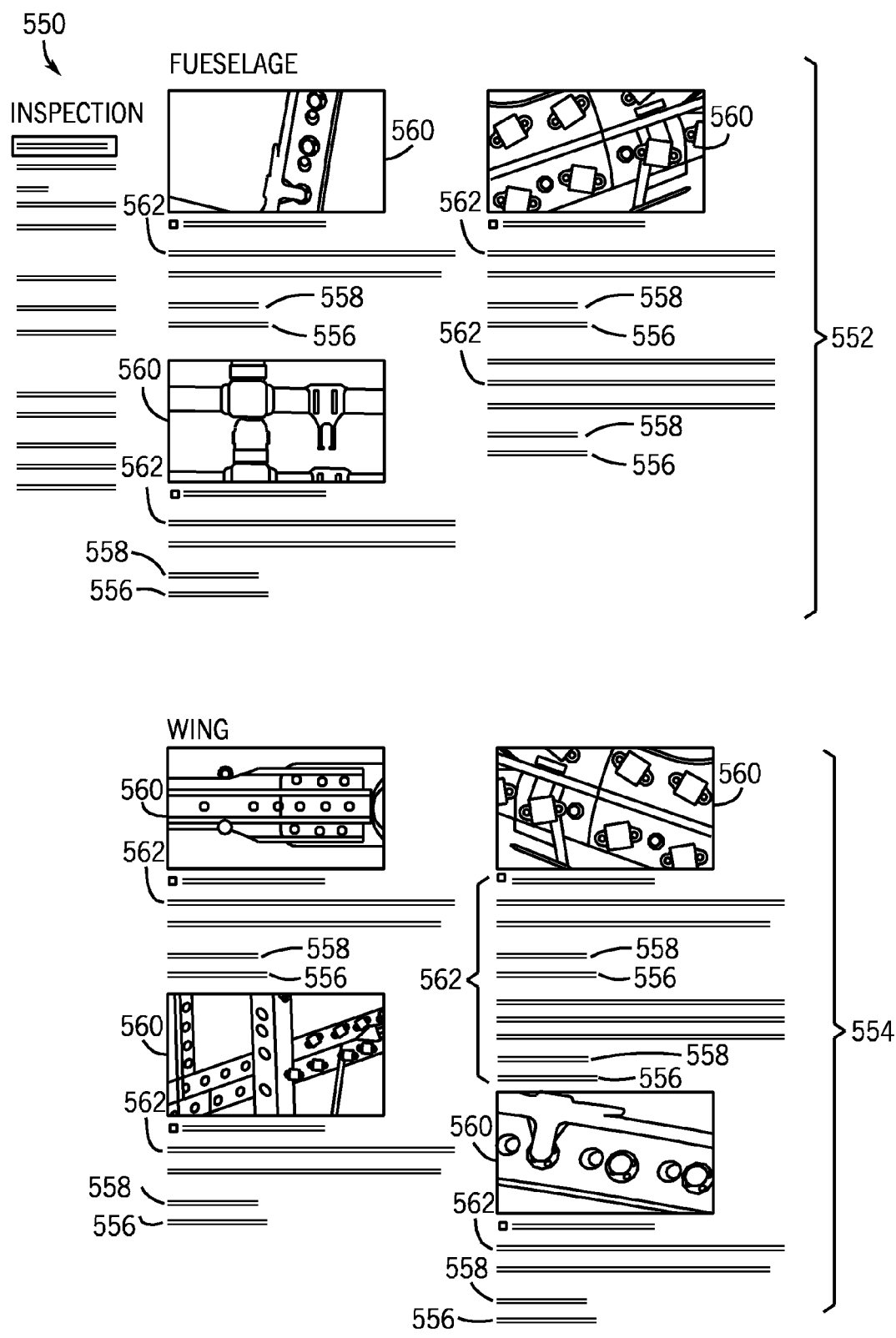
FIG. 18 is an example of filtered data obtained based upon the selections made in FIG. 17, in accordance with an embodiment.

For efficiency, some inspectors or other personnel may desire to make multiple selections in the graphical filter. FIG. 17 is an example of selecting both the wing graphical filter element 502 (as indicated by the pointer 504) and the fuselage graphical filter element 506 (as indicated by the pointer 508) from the presentation model 500 to obtain specific inspection data for each of these components, in accordance with an embodiment. Upon selecting these elements 502 and 506, the system queries the data source for inspection data relating to either of these components. The data source returns the inspection data for these components, where they are presented to the inspector or other personnel. For example, FIG. 18 illustrates an inspection report 550 that provides the fuselage inspection data 552 as well as the wing inspection data 554. As with the other inspection reports, all pertinent inspection data may be provided in the inspection report 550. For example, the report 550 may include inspection dates 556, names 558 of the inspector(s)

completing the inspection, images 560, notes 562, and any other pertinent inspection data.

As may be appreciated, the current application provides efficient systems and methods for presenting inspection data through use of a graphical filter. By using the graphical filter, inspectors and/or other personnel may efficiently and easily understand the current inspection status for a particular object. Further, the inspector or other personnel may access the inspection data in a very easy manner using a particular graphical representation of the inspected object, thus reducing the complexity in obtaining particular data for a specific sub-component of the inspected object. Accordingly, This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
    obtaining, via a processor, a computer-presentable model relating to an object being inspected;
    determining, via the processor, a portion of the computer-presentable model relating to a portion of the object to be inspected;
    inspecting, via an inspection tool, the portion of the object to gather inspection data;
    associating, via the processor, the inspection data with metadata comprising an indication of the portion of the model;
    displaying a graphical-user-interface, via an electronic display, wherein the graphical-user interface comprises:
        the computer-presentable model; and
        a graphical indicator displayed in an associated manner, by providing a graphical indication associated with the portion of the model, as indicated by the metadata, wherein the graphical indicator indicates that inspection data associated with the portion of the model is available for presentation upon subsequent selection of the graphical indicator, the portion of the model, or both, without presenting the inspection data until the subsequent selection is detected;
    detecting, via the processor, the subsequent selection of the graphical indicator, the portion of the model, or both; and
    after detecting the subsequent selection, displaying the inspection data via the graphical-user-interface.

2. The method of claim 1, wherein the computer-presentable model is a generic model associated with the object, wherein the generic model provides basic features of the object.

3. The method of claim 1, wherein the computer-presentable model is a specific model associated with the object, wherein the specific model provides detailed features of the object.

4. The method of claim 1, wherein associating the indicator of the portion of the model with the gathered inspection data comprises defining a relationship in a database between at least the indicator of the portion of the model and the gathered inspection data.

5. The method of claim 1, wherein associating the metadata with the gathered inspection data comprises appending a relational attribute to a file containing the model, the portion of the model, the gathered inspection data, or any combination thereof.

6. A system, comprising:
    computer-readable storage configured to store non-destructive testing inspection data relating to a portion of an object that has been inspected and metadata associated with the non-destructive testing inspection data, the metadata indicating the portion of the object;
    a processor configured to:
        present, via a graphical-user-interface of an electronic display, a model associated with the object;
        identify a portion of the model based upon the metadata;
        present a graphical indicator at the portion of the model, indicating that the inspection data relating to the portion of the object is available for presentation upon subsequent selection of the graphical indicator, the portion of the model, or both, without presenting the inspection data until the subsequent selection is detected;
        detect, via the graphical-user-interface, the subsequent selection of the graphical indicator, the portion of the model, or both; and
        after detecting the subsequent selection, displaying the non-destructive testing inspection data via the graphical-user-interface.

7. The system of claim 6, wherein the model associated with the object is a generalized model that provides basic features of the object; and wherein the processor is configured to present the indication on the generalized model.

8. The system of claim 6, wherein the model comprises a two-dimensional (2D) or three-dimensional 3D model.

9. The system of claim 6, wherein the processor is configured to alter the graphical indicator to provide an indication on the model of an amount of inspection data available for each portion of the object, without displaying the inspection data available for each portion of the object.

10. The system of claim 6, wherein the processor is configured to alter the graphical indicator to provide an indication of a characteristic of the inspection data.

11. The system of claim 10, wherein the characteristic comprises the freshness of the inspection data.

12. The system of claim 6, wherein the indication comprises a wire frame, an indication icon, or any combination thereof.

13. The system of claim 6, wherein the processor is configured to alter the graphical indicator by changing a color of the graphical indicator.

14. The system of claim 6, wherein the indication comprises a wire frame and the processor is configured to alter a wire frame thickness, a spacing of the wire frame, or both, to illustrate a freshness of the inspection data, an amount of inspection data, or both.

15. A tangible, non-transitory, machine-readable medium, comprising machine-readable instructions to:
    present, via a graphical-user-interface of an electronic display, a model associated with an object;
    retrieve non-destructive testing inspection data relating to a portion of the object that has been inspected from the machine-readable medium, wherein the inspection data is associated with metadata that indicates a portion of the object;
    identify the portion of the object using the metadata;

present, via the graphical-user-interface, at a portion of the model that represents the portion of the object, a graphical indicator that provides an indication of availability of the inspection data pertaining to the portion of the object for presentation upon subsequent selection of the graphical indicator, the portion of the model, or both, without presenting the inspection data until the subsequent selection is detected;

detect, via the graphical-user-interface, the subsequent selection of the graphical indicator, the portion of the model, or both; and after detecting the subsequent selection, displaying the non-destructive testing inspection data via the graphical-user-interface.

16. The machine-readable medium of claim 15, comprising instructions to alter the graphical indicator based upon a characteristic of the data.

17. The machine-readable medium of claim 16, comprising instructions to alter a color of the indication.

18. The machine-readable medium of claim 15, comprising instructions to present a label with the graphical indicator, the label providing supplemental information about the graphical indicator.

19. The machine-readable medium of claim 15, comprising instructions to present a variation map representative of relative variances in the inspection data.

20. The machine-readable medium of claim 15, comprising instruction to:
   determine a criticality of the non-destructive testing inspection data;
   present the graphical indicator in a first color when the criticality is low; and
   present the graphical indicator in a second color, different from the first color, when the criticality is high.

* * * * *